US011865327B1

(12) United States Patent
Biddell

(10) Patent No.: US 11,865,327 B1
(45) Date of Patent: Jan. 9, 2024

(54) SYSTEM AND METHOD FOR IDENTIFYING ORGANELLES AND TISSUE TYPES OF THE BRAIN USING REPRESENTATIVE FREQUENCY SIGNATURES

(71) Applicant: Kevin M Biddell, Akron, OH (US)

(72) Inventor: Kevin M Biddell, Akron, OH (US)

( * ) Notice: Subject to any disclaimer, the term of this patent is extended or adjusted under 35 U.S.C. 154(b) by 1519 days.

(21) Appl. No.: 16/005,660

(22) Filed: Jun. 11, 2018

Related U.S. Application Data

(60) Provisional application No. 62/517,508, filed on Jun. 9, 2017.

(51) Int. Cl.
*A61N 1/36* (2006.01)
*A61B 5/00* (2006.01)
(Continued)

(52) U.S. Cl.
CPC .......... *A61N 1/36139* (2013.01); *A61B 5/316* (2021.01); *A61B 5/374* (2021.01);
(Continued)

(58) Field of Classification Search
CPC ............ A61N 1/36139; A61N 1/36196; A61N 1/36067; A61B 5/374; A61B 5/316; A61B 5/7264; A61B 5/7257
See application file for complete search history.

(56) References Cited

U.S. PATENT DOCUMENTS 6,449,603 B1  9/2002  Hunter
6,567,690 B2  5/2003  Giller
(Continued)

OTHER PUBLICATIONS

Kevin M Biddell, George T Mandybur, Hybrid Automated Computer Program for Localization of STN Borders during DBS Surgery, Minnesota Neuromodulation Symposium Poster, Apr. 16-17, 2015, Minneapolis, Minnesota.
(Continued)

*Primary Examiner* — Lindsey G Wehrheim

(57) ABSTRACT

A system and method for calculating representative frequency signatures for target regions of the brain. The method includes aggregating representative classified microelectrode recordings taken from regions of the brain of multiple patients to an initial database. The classified microelectrode recording data is then transformed into the frequency domain. Frequencies profiles, grouped according to each target region of the brain they represent, are stored in a database. A coherence or Z-score representing the prominence of a frequency with respect to other frequencies within a group of frequencies profiles for each target region of the brain they represent is then calculated and stored, as well as the average power of the frequencies within the group of frequency profiles. Redundant frequencies or frequencies above or below pre-determined thresholds are removed from the group of frequency. The resulting representative frequency signature for each target region of the brain is stored as a group of frequencies, a coherence or Z-score and an average power of the respective frequencies. During a DBS surgery, the desired representative frequency signature file(s) representing target regions of the brain are selected, which representative frequency signature file(s) include a list of frequencies, their respective powers, and Z-scores. During DBS surgery, real time microelectrode recordings of brain signals from a patient are obtained, and the powers of frequencies of the real time microelectrode recordings are calculated at frequencies found in the signatures. The calculated powers of frequencies of the real time microelectrode recordings are compared to the respective powers in the pre-selected representative frequency signature files, and a percent error via the commonly accepted method, and averaging the group of errors via the commonly accepted root mean square calculation is calculated. A (Continued)

negative averaged percent error over time is plotted and displayed as a measure of frequency signature strength in order to detect movement of the stimulating electrode being implanted with respect to the target region of the brain.

12 Claims, 16 Drawing Sheets

(51) Int. Cl.
    *A61B 5/374*     (2021.01)
    *A61B 5/316*     (2021.01)
(52) U.S. Cl.
    CPC ........ *A61B 5/7264* (2013.01); *A61N 1/36196* (2013.01); *A61B 5/7257* (2013.01); *A61N 1/36067* (2013.01)

(56) References Cited

U.S. PATENT DOCUMENTS

| | | |
|---|---|---|
| 7,167,760 B2 | 1/2007 | Dawant et al. |
| 8,078,281 B2 | 12/2011 | Priori |
| 8,280,514 B2 | 10/2012 | Lozano |
| 8,591,392 B2 | 11/2013 | Bentwich |
| 8,606,740 B2 | 12/2013 | Danish |
| 8,798,755 B2 | 8/2014 | Grill |
| 8,849,392 B2 | 9/2014 | Lozano |
| 9,037,224 B1 | 5/2015 | Fu |
| 9,220,458 B2 | 12/2015 | Pouratian |
| 9,235,685 B2 | 1/2016 | McIntyre et al. |
| 9,247,890 B2 | 2/2016 | Turnbull |
| 9,326,698 B2 | 5/2016 | Blanco |
| 9,326,725 B2 | 5/2016 | Finkle |
| 9,498,628 B2 | 11/2016 | Kaemmerer |
| 9,572,988 B2 | 2/2017 | Grill |
| 9,728,111 B2 | 8/2017 | Guo et al. |
| 9,842,391 B2 | 12/2017 | Tunstall |
| 10,004,902 B2 | 6/2018 | Moffitt |
| 2007/0167856 A1* | 7/2007 | McNames ............... A61B 5/24 600/544 |
| 2010/0191695 A1 | 7/2010 | Danish |
| 2014/0094823 A1 | 4/2014 | Carcieri |
| 2014/0148657 A1* | 5/2014 | Hendler ............... A61B 5/291 600/545 |
| 2014/0163627 A1 | 6/2014 | Starr |
| 2014/0358024 A1 | 12/2014 | Nelson |

OTHER PUBLICATIONS

Telkes, I., Jimenez-Shahed, J., Viswanathan, A., Abosch, A., & Ince, N. F. (2016). Prediction of STN-DBS electrode implantation track in Parkinson's disease by using local field potentials. Frontiers in Neuroscience, May 10, 1-16. https://doi.org/10.3389/fnins.2016.00198.

Valsky, D., Marmor-Levin, O., Deffains, M., Eitan, R., Blackwell, K. T., Bergman, H., & Israel, Z. (2017). Stop! border ahead: Automatic detection of subthalamic exit during deep brain stimulation surgery. Movement Disorders, 32(1), 70-79. https://doi.org/10.1002/mds.26806.

Garonzik et al., Intraoperative microelectrode and semi-microelectrode recording during the physiological localization of the thalamic nucleus ventral intermediate, Movement Disorders 17, Issue Supplement 3, S135-S144 (2002).

Hutchison et al., Neurophysiological identification of the subthalamic nucleus in surgery for Parkinson's disease, Annals of Neurology 44:4, 622-628 (1998).

Chaovalitwongse et al., Pattern recognition approaches for identifying subcortical targets during deep brain stimulation surgery, Intelligent Systems, IEEE 26:5, 54-63 (2011).

Wong et al., Functional localization and visualization of the subthalamic nucleus from microelectrode recordings acquired during DBS surgery with unsupervised machine learning, Journal of Neural Engineering 6(2), 026006 (2009).

Afshar, P., Khambhati, A., Stanslaski, S., Carlson, D., Jensen, R., Linde, D., . . . Denison, T. (2012). A translational platform for prototyping closed-loop neuromodulation systems. Frontiers in Neural Circuits, Jan. 6, 117. https://doi.org/10.3389/fncir.2012.00117.

Moran, A., Bar-Gad, I., Bergman, H., & Israel, Z. (2006). Real-time refinement of subthalamic nucleus targeting using Bayesian decision-making on the root mean square measure. Movement Disorders, 21(9), 1425-1431. https://doi.org/10.1002/mds.20995.

Novak, P., Przybyszewski, A., Barborica, A., Ravin, P., Margolin, L., & Pilitsis, J. (2011). Localization of the Subthalamic Nucleus in Parkinson Disease Using Multi Unit Activity. J Neurol Sci., 310, 44-49. https://doi.org/10.1016/j.jns.2011.07.027.

Rajpurohit, V., Danish, S. F., Hargreaves, E. L., & Wong, S. (2015). Optimizing computational feature sets for subthalamic nucleus localization in DBS surgery with feature selection. Clinical Neurophysiology, 126(5), 975-982. https://doi.org/10.1016/j.clinph.2014.05.039.

Shamir, R. R., Zaidel, A., Joskowicz, L., Bergman, H., & Israel, Z. (2012). Microelectrode recording duration and spatial density constraints for automatic targeting of the subthalamic nucleus. Stereotactic and Functional Neurosurgery, 90 (5), 325-34. https://doi.org/10.1159/000338252.

Snellings, A., Sagher, O., Anderson, D. J., & Aldridge, J. W. (2009). Identification of the subthalamic nucleus in deep brain stimulation surgery with a novel wavelet-derived measure of neural background activity. Journal of Neurosurgery, 111(4), 767-74. https://doi.org/10.3171/2008.11.JNS08392.

Wong, S., Hargreaves, E. L., Baltuch, G. H., Jaggi, J. L., & Danish, S. F. (2012). Depth-time interpolation of feature trends extracted from mobile microelectrode data with kernel functions. Stereotactic and Functional Neurosurgery, 90 (1), 51-8. https://doi.org/10.1159/000334494.

Zaidel, A., Spivak, A., Shpigelman, L., Bergman, H., & Israel, Z. (2009). Delimiting subterritories of the human subthalamic nucleus by means of microelectrode recordings and a hidden Markov model. Movement Disorders, 24 (12), 1785-1793.https://doi.org/10.1002/mds.22674.

\* cited by examiner

Figure 4.

CLIPS — 401
- REC_ID
- PATIENT_ID
- SIDE
- TRAJECTORY
- FILE_NAME
- DEPTH

SYMPTOM_HISTORY — 402
- ORDER
- PATIENT_ID
- AGE
- FIRST_AWARENESS
- SECOND_AWARENESS
- SECOND_SYMPTOM
- FIRST_SYMPTOM
- BODY_PART_I
- REFINEMENT
- BODY_PART_II
- SIDE_II
- SIDE_I
- PRE_SURG_UPDRS_ON
- PRE_SURG_UPDRS_OFF
- DATE_DX
- YEARS_DISEASE
- SURGERY
- DATA_NOTES

REGION_OF_INTEREST — 403
- REC_ID
- PATIENT_ID
- SIDE
- TRAJECTORY
- FILE_NAME
- DEPTH
- REGION
- TIME_BEGIN
- TIME_END
- METHOD
- METHOD_DETAIL_I
- METHOD_DETAIL_II
- UPPER_THRESHOLD
- LOWER_THRESHOLD
- DATE_ADDED
- DATE_MODIFIED
- PHASE
- 1stSIDE

FILES_OF_INTEREST — 404
- REC_ID
- PATIENT_ID
- SIDE
- TRAJECTORY
- FILE_NAME
- DEPTH
- REGION
- PHASE
- TIME_BEGIN
- TIME_END
- ISIDE

DISTINCT_MICRO_ELECTRODE_NOTES — 405
- ID
- PATIENT_ID
- PENETRATION
- SIDE_ORDER
- SIDE
- CANNULA_HOLE
- ENTER_STN
- EXIT_STN
- STN_SPAN
- MICRO_DRIVE_DEPTH
- IMPEDENCE_BRAIN
- NOTE_LOCATION
- NOTE_QUALIFIER
- RECORDING_NOTES
  - RECORDING_NOTES.Value
- STIM_RESPONSE_1
- STIM_RESPONSE_1_QUALIFIER
- STIM_RESPONSE_2
- STIM_RESPONSE_2_QUALIFIER
- PATIENT_NOTES

NEUROLOGY_SURGICAL_NOTES — 406
- PATIENT_ID
- UC_MEDICAL_REC_NUM
- DOC_BARCODE
- NAME_LAST
- NAME_FIRST
- NAME_MI
- GENDER
- BIRTHDATE
- SURGERY_DATE
- AC_PC_LINE
- LATERAL
- POSTERIOR
- INFERIOR
- PASS

Figure 5.

STN DBS INTRAOPERATIVE ELECTRODE RECORDING NOTES

| LAST NAME | FIRST NAME | SURGERY DATE | DB PATIENT ID |
|---|---|---|---|
| Doe | Jon | 3/4/2015 | 2 |

SIDE- LEFT    ORDER- SECOND

Penetration #- 1    Imp. (brain)- 120    CANNULA HOLE- RIGHT

| DRIVE DEPTH | RECORDING NOTES | | RESPONSE TO STIM | | | |
|---|---|---|---|---|---|---|
| 1 | | | | | | |
| 2 | | | | | | |
| 2.2 RED NUCLEI | Possibly | exit | YES | elbow | | |
| 5 OPTIC TRACT | Probably | high amplitude | YES | shoulder | NO | nose |
| 6 | | | | | | |
| 7 Gpe hi | Possibly | intermittent bursting | | | | |
| 8 | | | | | | |
| 8 SNR | Definitely | very quiet, exit | | | | |
| 9 | | | | | | |
| 9 STN | Probably | transient | | | | |
| 9 THALAMIC | Possibly | very quiet | | | | |
| 9.1 THALAMIC | Possibly | very quiet | | | | |
| 10 | Possibly | scattered activity | | | | |
| 10 STN | Definitely | transient | | | | |
| 29 Gpe | Possibly | end of recording | YES | shoulder | NO | nose |

| EXIT STN (mm) 30 | ENTER STN (mm) 25 | Stn Span (mm) 5.00 |
|---|---|---|

Surgery Date- 3/4/2015    02249356    MALE    7/24/1951
Doe    Jon    D    103122290

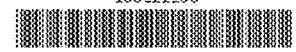

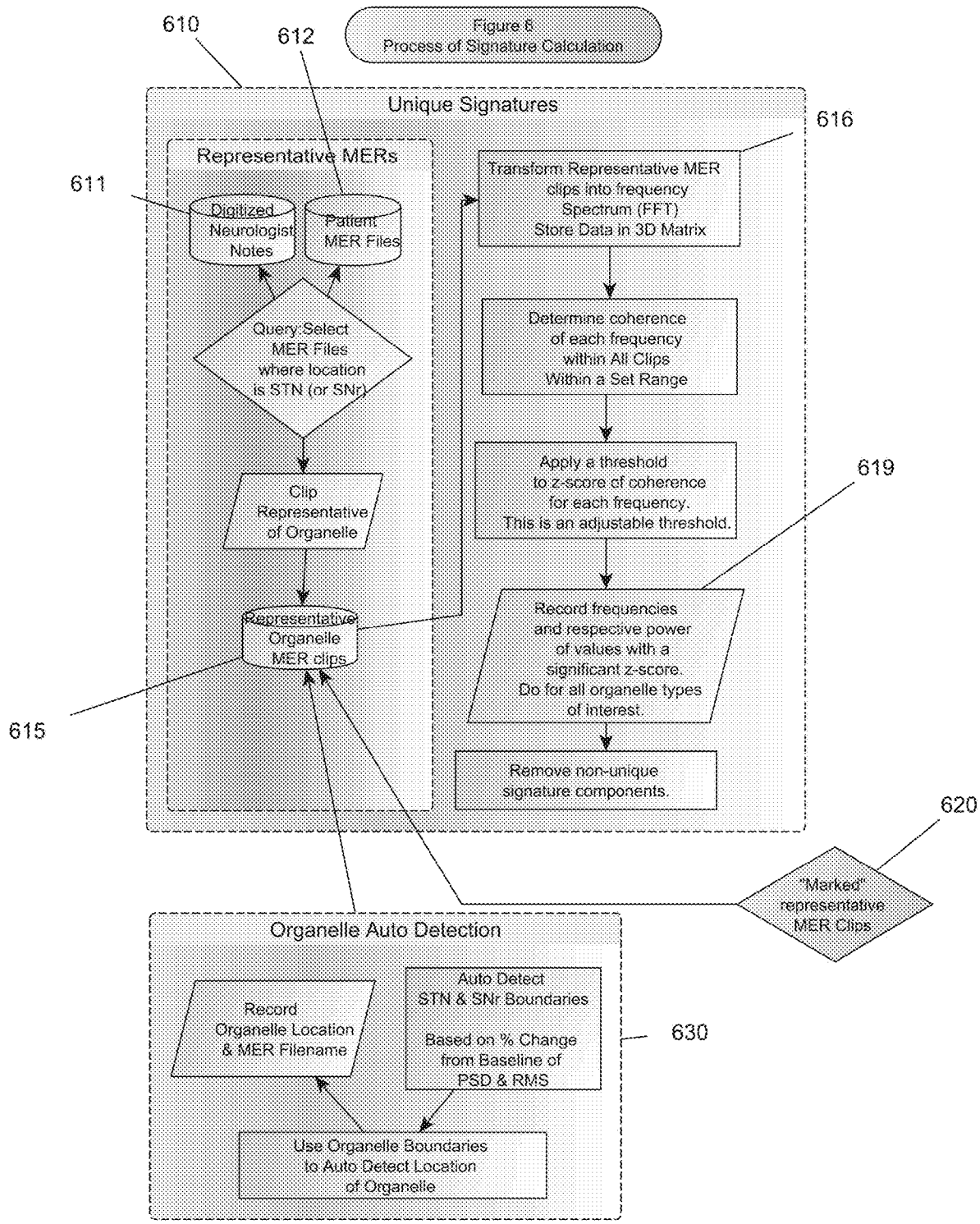

Figure 12

Mathematics of "Signature Differences" Tool

[1*] If $C(fx)_{sigA} <= C_o$ then $sigA(fx) = 0$

[2*] If $P(fx)_{sigA} <= P_o$ then $sigA(fx) = 0$

[3*] If $C(fx)_{sigA} >> C(fx)_{sigB}$ then $sigA(fx) = [P(fx)_{sigA}, C(fx)_{sigA}]$ ; $sigB(fx) = 0$

[4*] If $P(fx)_{sigA} >> P(fx)_{sigB}$ then $sigA(fx) = [P(fx)_{sigA}, C(fx)_{sigA}]$ ; $sigB(fx) = 0$

[5*] if $C(fx)_{sigA} \sim>> C(fx)_{sigB}$ && $P(fx)_{sigA} \sim>> P(fx)_{sigB}$ then

[5a*] If $(P(fx)_{sigA} * C(fx)_{sigA} - P(fx)_{sigB} * C(fx)_{sigB}) <= M_o$ then $sigA(fx) = sigB(fx) = 0$

[5b*]Else $sigA(fx) = [P(fx)_{sigA}, C(fx)_{sigA}]$; $sigB(fx) = 0$ $C_o$ means the preset Coherence score threshold value; (0.2) is used, but it can range from (0.1) to (0.9).

$P_o$ means the preset Power threshold value; (3) is used, but it can range from (1) to (1000).

"fx" means a frequency value x.

"sigA" means the signature of substructure A.

"sigA(fx)" means the signature of substructure A at fx.

"sigA(fx)=0" means the signature of substructure A at fx is set to 0 (i.e., $sigA(fx) = [P(fx)_{sigA}, C(fx)_{sigA}] = 0$).

"$P(fx)_{sigA}$" means the Power of signature A at fx.

"$C(fx)_{sigA}$" means Coherence Score of signature A at fx.

"==" means logical check for equality.
"~=" means logical check for not equal.

">=" means logical check for greater than or equal.
"<=" means logical check for less than or equal.

">>" means a logical check for MUCH greater than (i.e., $A >= M_o * B$).
"~>>" means a logical check for NOT MUCH greater than (i.e., $M_o * B > A > B$).

"<<" means a logical check for MUCH less than (i.e., $A <= (1/M_o) * B$).
"~<<" means a logical check for NOT MUCH less than (i.e., $(1/M_o) * B < A < B$).

"&&" means a union (AND) in a logical check.

$M_o$ means the preset Multiplication similarity threshold; (3) is used, but it can range from (2) to (25).

"*" indicates that the converse of the rule is used as well (i.e. swap A and B in the rule).

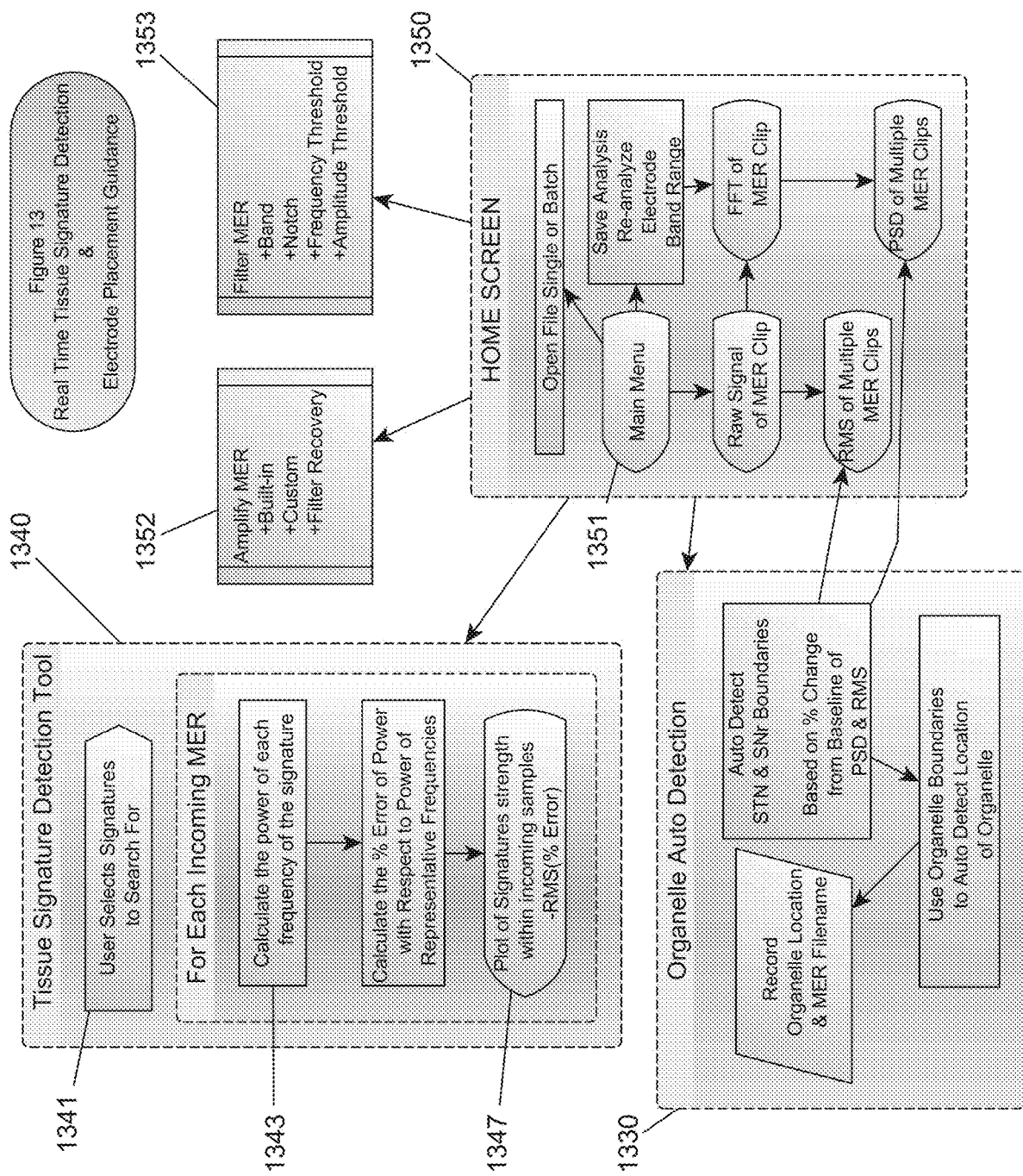

SYSTEM AND METHOD FOR IDENTIFYING ORGANELLES AND TISSUE TYPES OF THE BRAIN USING REPRESENTATIVE FREQUENCY SIGNATURES

CROSS-REFERENCE TO RELATED APPLICATIONS

This application claims priority from U.S. Provisional Application Ser. No. 62/517,508 filed Jun. 9, 2017, which is incorporated herein by reference.

FIELD OF INVENTION

This application relates to identification of brain organelles and tissue types, and more specifically to a system for such identification using representative frequency signatures.

BACKGROUND

Deep brain stimulation (DBS) for controlling the symptoms of Parkinson's disease has been approved by the Food and Drug Administration (FDA) of the U.S. government for over 15 years. Several well-conducted studies show significant impact of high frequency electrical stimulation of the sub-thalamic nucleus (STN) of the brain to reduce Parkinson's disease symptoms. Much research has been done over the years on the localization of the sub-thalamic nucleus during DBS surgery, for example, as in U.S. Pat. Nos. 7,167,760, 8,606,740 and 9,220,458. Some research has focused on using microelectrode recordings (MER) to automatically detect the pre-sub-thalamic and post-sub-thalamic nucleus boundaries. The most successful approach has been research grounded in determining the power spectral density of the beta band frequency (15-35 Hz) of the MER using a guidance system add-on feature. However, such an approach is believed to be insufficient to accurately detect the STN, and in particular, it is believed that the red nucleus of the brain may be mistaken for the STN using these research parameters.

Unfortunately, the research in DBS has not translated into significant changes in the standard of care. DBS surgery in humans is being performed routinely with probe placement being guided by MER. Experienced physicians/surgeons "listen" to the digital signals generated and make empirical decisions, including final placement of the stimulating electrode. Though there are only a few studies that show the benefit of this technique, as opposed to simply placing the electrodes via direct MRI targeting, it is believed that more can be learned from MER using digital processing. While software has been developed which uses localization algorithms to automatically detect boundaries of the sub-organelles in the basal ganglia during DBS probe placement surgery; see Biddell, K. M., Mandybur, G. T. (2015, April). *Hybrid Automated Computer Program for Localization of STN Borders during DBS Surgery*. Poster presented at the Minnesota Neuromodulation Symposium, Minneapolis, MN; improved techniques to more accurately characterize and distinguish the various organelle tissue types in the brain are needed to further improve the results of DBS and electrode placement.

SUMMARY

The present application provides a system and method for generating representative, unique, frequency signatures for various organelles, including the sub-thalamic nucleus, of the human brain. The generated representative frequency signatures may then be used to improve medical treatments by enabling improved target identification of organelles and for placement of electrodes within the brain. Such improved identification provides recognition of brain tissues or organelle types being approached, entered, or exited by real time tissue detection using the microelectrode recording data being detected.

The process for calculating or generating representative frequency signatures involves aggregating representative microelectrode recordings from multiple patients. The MER files or data are obtained during electrode placement surgeries for deep brain stimulation therapy from patients with Parkinson's disease or other movement disorders. The MER data obtained from patients are classified according to the various tissue types or organelles, STN, SNr, RN, etc., from which they were recorded. Several options may be provided for classifying MER data: 1) Intra-operative digitized notes of the health care provider; 2) Automatic border detection algorithms; and 3) Retrospective "marking" of exemplary recordings.

The MER data is classified using the desired option, and preferably by retrospective "marking" of the exemplary recordings. Using the signature calculation tool, a MATLAB program, the classified representative MER data is further transformed into the representative frequency domain, for example, using a Fourier transform. The frequency profiles representing the particular type of organelle or tissue being characterized are stored in the database of all the transformed data. The coherence—or Z-scores—of all the frequencies within a selected range, for a given tissue type, is then calculated and stored. The Z-score is a measure of how prominent or common a given frequency is with respect to other frequencies.

Using the Signature Calculation tool, frequency values with Z-scores below a predetermined reasonable threshold are removed as unnecessary. Other unneeded or redundant frequency values are removed, such as 60 Hz "noise" and related harmonic multiples. An automatic signature difference tool may also be used to automate the removal of unneeded or redundant frequency values.

Using the Signature Calculation tool, a unique representative frequency group or frequency signature for each organelle or tissue type is identified and stored within a file. Each unique representative frequency signature consists of three (3) component values: a group of frequencies, their Z-scores, and their average powers. The unique representative frequency signature for each different tissue type or organelle is then available for use in various software, system and method applications for improving a variety of individual medical treatments by providing more accurate signature detection information regarding the location and state of various organelles within the brain.

Once the Signature Calculation tool establishes a set of representative frequency signatures for each tissue type or organelle, a neurology team preparing for DBS electrode placement surgery for an individual patient initializes the Tissue Signature Detection tool by pre-selecting the frequency signature file(s) representing the targeted and surrounding tissue types or organelles for detection. During the DBS surgery, the patient's incoming MER data is processed real time using the Tissue Signature Detection (TSD) tool, which is a MATLAB® program that uses the uploaded or stored frequency signature file(s). The uploaded frequency signature file(s) include a list of frequencies and the respective powers. The respective powers are compared by the TSD tool to the calculated powers of the corresponding frequencies in the incoming MER data. The Tissue Signature Detection tool uses a percent error calculation as the comparison technique. To illustrate the frequency signature strength, or closeness to the targeted tissue type, the percent error is averaged, via Root Mean Squares (RMS), and the negative RMS of percent error is plotted. Plotting the average percent error over time reveals an increase or decrease in signature strength as the electrode travels toward or away from the tissue type or target of interest. The resulting plot assists the neurology team's decision making process, and confirms movement of the electrode in a direction closer or farther away from the surgical target.

The present application has other features and advantages which will be apparent from or are set forth in more detail in the accompanying drawings, which are incorporated herein, together with the following detailed description.

BRIEF DESCRIPTION OF THE DRAWINGS

FIG. 4 illustrates sample computer screen captures of available tables for storing various categories of MER data collected during DBS electrode placement surgery.

FIG. 5 illustrates a computer screen capture of a sample digital report of notes entered into the sample table of Neurology Surgical Notes shown in FIG. 4, of which the notes may be used for classification of the MER data.

FIG. 6 schematically illustrates a flow chart showing the process steps of the present application for calculating representative frequency signatures.

FIG. 12 illustrates mathematical steps used by the automatic Signature Difference tool within the Signature Calculation tool.

FIG. 13 schematically illustrates a flow chart showing the process steps of the present application using the Tissue Signature Detection tool.

DETAILED DESCRIPTION

Figure 1:
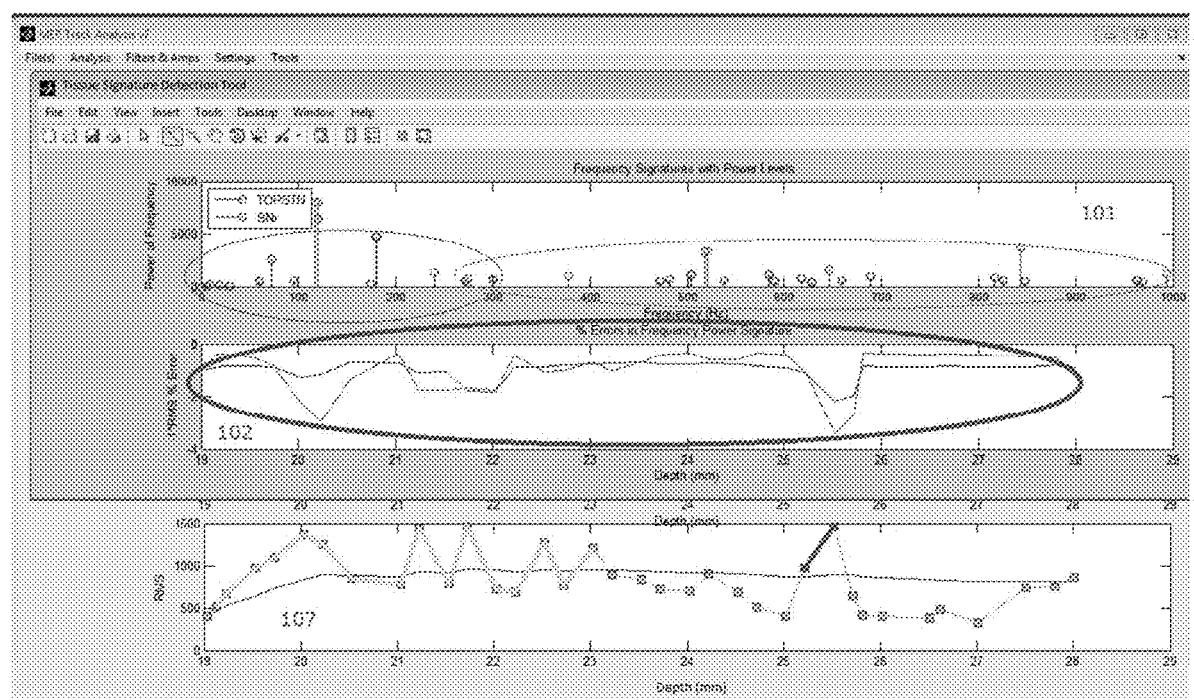
FIG. 1 illustrates sample computer summary screen capture showing use of the Tissue Signature Detection (TSD) tool of the present application.

The following detailed description includes references to the accompanying drawings, which form a part of the detailed description. The drawings show, by way of example, specific embodiments in which the invention may be practiced. These embodiments, which are also referred to as examples, are described in sufficient detail to enable those skilled in the art to practice the embodiments. The embodiments may be combined, other embodiments may be utilized, or structural and logical changes may be made without departing from the scope of the present invention. The following description is intended as illustrative only, with the scope being defined by the claims and their equivalents. As used in this application, the terms "a," "an" and "the" include one or more than one. The term "or" refers to a nonexclusive or, unless otherwise indicated. The term "in" includes "in" or "on" unless otherwise indicated. Generally, the terms used in this application have their ordinary meanings in the art, within the context of the application, and within the specific context where the term is used. Additional specific terms are defined below.

The term "disease" includes, but is not limited to, epilepsy, Huntington's disease, Parkinson's disease and related movement disorders, Alzheimer's disease and related memory disorders, ALS, muscular dystrophy, dystonia and depression.

The term "target" refers to the desired neural structures, organelles or tissue types within the brain where a physician desires to locate or implant a stimulating electrode.

In the present application, it is understood that the specific tissue type from organelles in each human or patient's brain produces a similar unique frequency set, having a universal characteristic pattern for the specific tissue type in each organelle. The frequency set is unique for each tissue type in each organelle, and universal from patient to patient. The detection of unique frequency signatures for distinguishing between the various organelle tissue types in the brain is accomplished by the process or method of this application which correlates collected or aggregated MER data at known locations of the brain. Later, the generated representative frequency signatures are compared with real time data collected by a health care provider/neurologist during an electrode placement/implant procedure/DBS surgery, to better inform placement of the electrode at a location where the real time microelectrode recording data includes the unique frequency signature of the desired target, organelle or tissue type.

The signature creation process starts with the MER data obtained during prior DBS surgeries for Parkinson's disease or other movement disorders. The MER data is first classified according to the tissue type from which they were recorded. It is understood that MER systems used in DBS surgery for gathering such data include, for example, the Guideline 4000 LP+™ system from FHC, www.fh-co.com; inomed ISIS Micro Electrode Recording system from inomed Medizintechnik GmbH, www.en.inomed.com; or the Neuro Omega system with the HaGuide assistance software from Alpha Omega Co. USA Inc., www.alphaomega-eng.com. Such commercially available systems are used by neurosurgeons during such electrode placement surgeries.

Frequency Signature Calculation

Generating frequency signatures that distinguish various organelle tissue types in the brain requires combining three sets of data: 1) neurology notes that record the location of the deep brain stimulation (DBS) drive system at multiple stopping points during surgery, 2) microelectrode recordings (MERs) from the DBS surgery, and 3) metadata from patients' pervious neurology visits and observations at the time of DBS surgery. The digitized neurology notes are collected in a note entry database, either entered on a computer during surgery or manually entered at a later time from handwritten notes that have been saved and/or scanned. The neurology notes contain references to the microelectrode recordings, the time of the recordings, and the distance into the brain. The neurologist labels where the team believes the tip of the microelectrode is located within the brain. This metadata designates representative microelectrode recordings (MERs) of tissue samples. The database is queried for all the MER files of the subthalamic nucleus (STN), substantia nigra reticulata (SNr), or any other organelle of interest labeled by the neurologist. The database software does the cross referencing and supplies records indicating the depth and file location for those clips that are representative of the tissue type. It is not software dependent; presently this is done in Microsoft® Access® but could be accomplished in Microsoft® SQL® or another other database software of preference. A list of representative clips is compiled in the database for that type of tissue for multiple patients.

To summarize, three databases are used—1) the recording data, 2) neurologist notes, and 3) data records that are a combination of the first two, storing the location of recordings from multiple patients for specific organelles. The third is a subset of the others, but it is its own database that is uniquely valuable and enables finding the representative MERs for a given organelle.

To classify the aggregated MER data as collected from a specific tissue type within the brain, several methods may be used, which are referenced here as a Signature Calculation tool. One method is to run a query, using the Applicants Signature Calculation tool, on the database of the MER clip metadata and the digitized neurology notes.

Another MER classification method uses Applicant's automatic border detection algorithm The algorithm is used in an automatic border detection software tool which considers the various "features" or characteristics identified in research literature for the STN and the substantia nigra reticulate (SNr) as detectable from microelectrode recordings, such as wavelet features, root mean square (RMS) and power spectral density. Research has shown that within the brain, there are differences in the power of specific frequency bands for the specific tissue types. The automatic border detection tool uses these power spectral density and RMS differences, and when a certain level or threshold is exceeded in the MER data, the automatic border detection tool signals that the microelectrode is in the STN or other organelle of interest. Since the substantia nigra *reticulata* is the subsequent organelle next to the STN, as the electrode moves during the DBS surgery, there is an interval of time and space between the STN and the SNr signals. After a drop in frequency and continuation without a frequency rebound, the electrode must be located within the SNr as noted by the characteristic frequencies of the MER signal data. Additionally, because the SNr is the next structure in the brain anatomy after the STN, once the SNr is entered it can be confirmed that the electrode has left the STN. The automatic border detection tool searches for the changes in character and progression of signals to determine the location of the electrode in the organelles of interest. In the improved MER Track Analysis Tool, upon identifying MER data within the region of interest or organelle of interest, the user is presented the option for the MER metadata to be saved in a separate database table. This newly added method of saving the metadata for "Regions of Interest" via easy buttons (312) and (314) is provided in FIG. 3.

Figure 3:
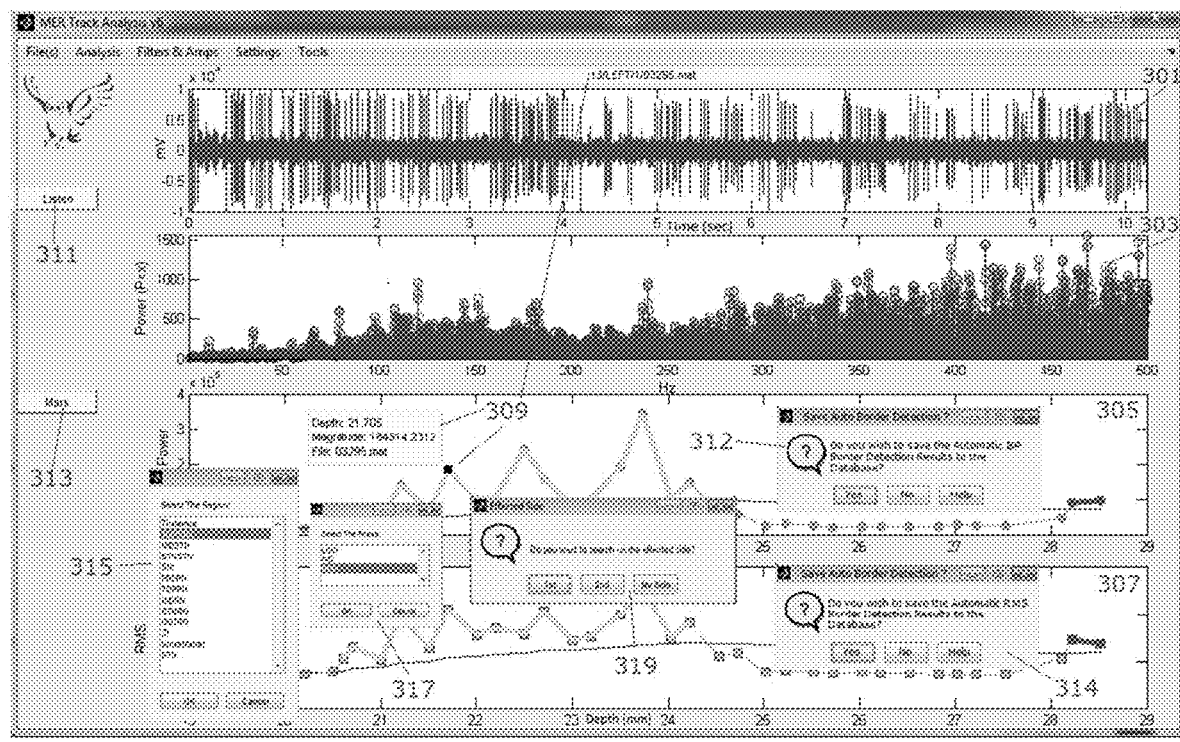
FIG. 3 illustrates sample computer screen captures of the marking tool and the user-interface for entering the results from the automatic detection methods into a custom database.

A third method of classification is provided in the computer implemented improved MER Track Analysis Tool, which provides a "Mark" button (313) in FIG. 3. Knowledgeable neurology health care providers conducting the DBS surgery and making the microelectrode recordings are often able to recognize the STN by MER signal—either visually on the MER system computer screen, or by a sound generated from the MER system computer speaker. If they are confident that a particular signal is an organelle of a particular type, they can click or select the "Mark" button in the MER Track Analysis software tool to mark this file accordingly and store the metadata in a Files of Interest database table (404). Still further, there are phases of low, middle and high amplitude neuron firing, as the neurons are not always firing, but can still be part of that certain tissue type. Such phase information may also be saved and stored as metadata in the MER Track Analysis database (404). A side of the organelle can also be labeled, if known, as a first or second side of the organelle affected by the disease. The terms first or second side represent the more affected side or lesser affected side, respectively. This data can also be saved and stored as metadata in the Files of Interest database table.

Of these three classification methodologies, using the "Mark" button to electronically mark the file is the most complete, thorough, and provides the finest resolution of the MER data. Using the Mark button allows the health care providers to conveniently classify the MER data by region, phase and first or second affected side, which is labeled and stored in the Files of Interest database. Storage of the file metadata in the Regions of Interest or Files of Interest database tables, as shown in FIG. 4, includes the referencing information but not the MER data itself, as the referencing information is sufficient for the tools to search for and retrieve the MER data.

Once the representative MER data is classified by organelle or tissue type and a database of MER clips has been collected that are characteristic recordings of the organelle sub-tissues of interests, they are transformed into the frequency domain. It is noted that the frequency signature is not dependent on time or the length of the MER data. The MER data, in the time domain, may be trimmed or edited to capture the unique behavior of the signal of the STN, with a focus on capturing the unique characteristic pattern of the tissue type recorded. The unique signature patterns are determined by taking the representative organelle MER data, in the time domain, and transforming them into their frequency domain, preferably using a fast Fourier transform (FFT). The use of the frequency domain is preferred, as there is no weighting between one set of data and another set of data based on time or the length of the MER data clip.

Once the set of frequencies and respective powers for each data set are calculated, a coherence algorithm is run to determine the given frequencies' commonality, the coherence function in the MATLAB program. The coherence is a value ranging from zero to one measuring how common that frequency is in the sets of recorded values. A one (1) indicates that a given frequency is in almost all of the recordings; a zero (0) indicates that it is not there at all. (A different scoring system could be used.) Then a threshold is applied and the scores that are low are dropped (those that are least common).

At first, it is desired to err on the side of having too many frequencies in the signature so that something that is unique is not removed. There is going to be some overlap between the signature of one tissue and a signature of an adjacent tissue. These organelles have common traits, as do their respective signatures. The goal is isolating a unique characteristic signature for each organelle.

The Z-score and the average power are calculated for each frequency in the MER clips. The Z-score does not embody everything needed to represent the underlying tissue's signal (only capturing the likelihood the given frequencies). A measure of power is needed. For example, if there is a frequency at a low power, as long as it is common for that signal to have the low power, then it gets a high Z-score. Therefore, the "Signature Calculation" tool also calculates and records the average of the powers for the given frequencies in the data. Both values are needed; the Z-score is used in generating the signature and the average power is used in detecting a particular organelle. Hence, the signature for a specific organelle is composed of three values: a list of frequencies, their Z-scores, and average powers.

This signature can be further refined by using another feature or functionality included in the software that allows one to superimpose and view the signatures on top of each other. Signatures can be compared to determine common and unique elements of the tissue's representative signature. Those elements that are common to both can then be extracted. The user can refine, take out, and add pieces to generate the frequency signatures. This functionality aids in discovering the common characteristics among different tissues and facilitates the modification of the representative frequency signatures to capture that uniqueness. There are different patterns and therefore unique signatures for the beginning, middle and end of the STN; therefore, the signatures can be even further refined based on physiology. It is noted that while the number of signatures possible to include may be within a range of 5 to 60. However, a more ideal range of selected signatures is in the range of 7 to 50, with the most optimal number being in the range of 12 to 30.

Once unique signatures are established and stored, some testing may be needed as it is important to do some investigation on whether one signature works better than another in detecting tissues. This reasonable due diligence allows for refinement toward achieving the highest quality and the most effective signatures. Although the signatures were developed for use in real time signature detection in electrode placement guidance, which is discussed in FIG. 13, there are a number of potential uses for these signatures (see Alternative Uses). The process does not have to be real time. Currently, much of the work is retrospective.

Method of Signature Detection

The real time Tissue Signature Detection (TSD) tool is presently supported by the microelectrode analysis software which plots the raw MER data and the frequency spectrum of the incoming signal. In addition, the microelectrode analysis software calculates and plots the real time cumulative power spectral density (PSD) and root mean square (RMS) of those signals. A continual display of that information gives meaning to the neurologist and the neurosurgeon. To use the real time signature detection tool, the neurologist, neurosurgeon, or neuro-physiologist selects pre-created signature file(s) representative of the tissue type they wish to search for (two or three is reasonable). During surgery, each new incoming MER would be processed by the program in real time, as they are recorded and uploaded.

The representative signatures are a list of frequencies with a respective power and coherence (Z-score). The tissue signature detection tool calculates the power of the incoming MER for each listed frequency of the signature. The percent error is calculated—the experimental value (power of the specific frequency for the incoming signal), minus the theoretical value (the respective signature frequency), divided by the experimental value multiplied by 100%. This is done for all the frequencies listed in the signature. The average (via the root mean square method) of the percent error; and then the negative percent error is representative of the signature strength, are calculated. The error of the signature powers is being calculated with respect to the incoming microelectrode recording powers, but the negative value would be interpreted as the strength. Then the signatures strength is plotted over time to show an increase or decrease as the electrode travels towards or away from the tissue of interest. If the user is probing for two or three of these signatures at the same time, it will be apparent when it leaves one and enters another. The unique signature strength for one tissue type will drop while the signature for the next tissue type that the electrode is approaching increases in strength. This process can be used to direct the neurosurgeon and determine whether the electrode is getting closer or farther away from the tissue(s) of interest, represented by the signatures they selected in the software. In a DBS surgery for the treatment of Parkinson's disease, the likely signatures selected would be the Thalamus, STN, and SNr.

Detailed Figure Explanation

FIG. 1 shows two examples of Applicant's unique representative frequency signatures (101) of regions of the brain, and a method of using those frequency signatures to detect and display the boundaries of target tissue types of interest (102). This method is used to guide a neurosurgical team during microelectrode placement surgery. FIG. 1 is a summary screen capture of this innovative method. Reference numeral 101 is a graphical display of a plot of two unique frequency signatures. One frequency signature for the top part of the sub-thalmaic nucleus (TOPSTN) is in blue; the major components are circled in blue emphasizing the majority of elements are at the beginning of the frequency spectrum. The second frequency signature, in green, is of the substantia nigra reticulate (SNr). Its major components are circled in green, predominantly at the end of the frequency spectrum.

The result of retrospectively running the Tissue Signature Detection tool on the entirety of a patient's microelectrode recordings is shown in 102 (Circled in red). What is shown in 102 is the negative of the root mean square (RMS) of the percent errors between the powers of the frequencies of the two signatures and the power of the incoming MER signal at the respective frequencies. The commonly used root mean square (RMS) or average is used in two different ways. Reference numeral 107 is a graphical display of the root mean square (RMS) of the microelectrode recording signal, this continual plot of the RMS at each recording depth is providing a simple indication of the signals' strength, as the electrode is advanced into the brain during a DBS surgery. The graph in 102 is stretched out and is seen in the context of the supporting MER Analysis Tool (107); this is done to reflect the correlation and connections between the strengths of the individual signatures and their recording depths. Sharp changes are indicative of a change in location. There is a significant decrease in the SNr signature strength at 19.7 mm (102). The automatic border detection algorithm (107) is signaling at that point (in yellow) entering the STN. There is another sharp change between 25 mm and 26 mm (102), which indicates switching out of the STN and into the SNr; this is also supported by the automatic border detection algorithm in red (107). The Tissue Signature Detection process can be used as a tool to verify when the electrode has entered, is still within, or exiting the organelle of interest.

Figure 2:
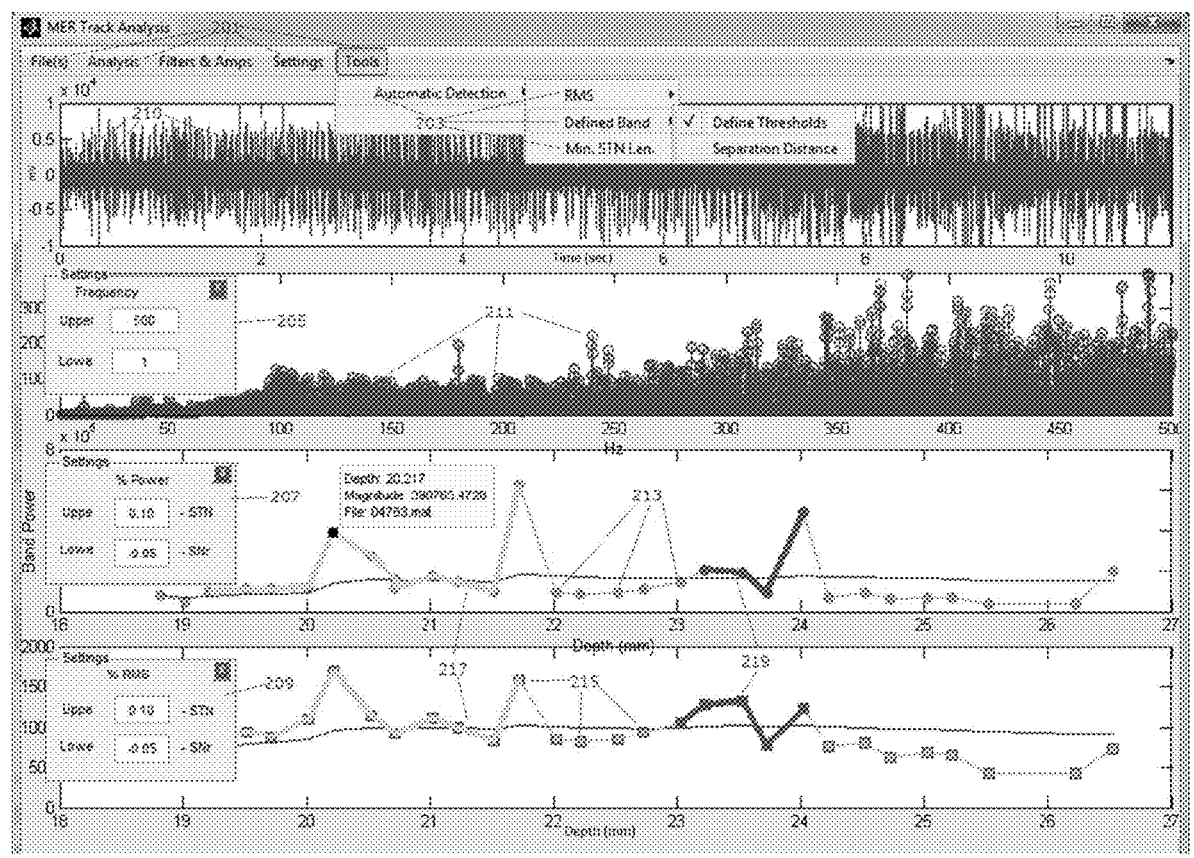
FIG. 2 illustrates a sample computer screen capture of a patient's raw MER data along with common analysis techniques used during a DBS surgery as the microelectrode is moved toward and beyond the target.

FIG. 2 shows a representation of a prior software tool that displays the raw MER signal, the power spectral density of a selected frequency band, and the continuous tracking as the microelectrode is advanced during surgery for an individual patient. Reference numeral 201 shows a selection of drop down tabs for accessing the different tools and graphical user interfaces (GUIs) to configure and run the program. A single "File" or selection of files can be chosen. Under the "Analysis" tab, a "New Analysis" option (not shown) clears the plots and erases previous work, allowing the user to start over. The "Settings" tab allows changes to variable settings, thereby enabling custom analyses. The "Filters and Amps" functions make it possible to filter or amplify the data in any number of ways; options include adding a notch filter or pass filter to clean the data. The "Settings" options include the ability to change the length of the recordings to use in the frequency transformation function (not shown). Multiple electrodes may be recorded during the surgery; the user can select which electrode recordings to process signals from. Other "tools" include the automatic border detection, the root mean square, and the defined band method algorithms.

At reference numeral 203 the graphical user interface (GUI) is shown which turns on the automatic border detection algorithm and its various options. "Automatic Detection", "Defined Band", and "Define Thresholds" are shown selected, and spawn GUI's 207 and 209. Reference numeral 203 also points to the ability to set the minimum length of the STN (a variable) used in the automatic border detection algorithm.

Selecting "Settings" from 201 allows the user to change the frequency band via the GUI at 205. In this example, the upper and lower bounds are 1 and 500 Hertz, respectively.

Reference numeral 207 displays the threshold settings of the band power method for the automatic border detection algorithm and 209 displays threshold settings for the root mean square (RMS) method of the automatic border detection algorithm. These threshold levels include variables to detect the STN and SNr. Other algorithm variables (not shown) can be set via the "Settings" tab.

Reference numeral 201 points to the patient's microelectrode (MER) signal display.

Number 211 demarcates three points in the power spectral density, for the signal in 210 with a band range set in 205.

The plot pointed to by reference numeral 213 displays the successive results of the summed band from 211. Each signal is recorded at their respective depths (mm) as the surgery progresses.

Number 215 is the RMS calculated for each microelectrode recording in 201, also at their respective depths (mm) as the surgery progresses.

Reference numeral 217 points to the automatic border detection algorithm results, based on the settings in 207 and 209. Shown in yellow is the automatic border detection's demarcation of the path of the subthalmic nucleus (STN).

In red, reference numeral 219 points to secondary results of the automatic border detection algorithm demarcating the substantia nigra reticulate (SNr).

FIG. 3 displays new aspects of software within the context of the foundational pieces from FIG. 2. 301 (210) is the microelectrode recording signal display. 303 (211) is the fast Fourier transform (FFT) of the signal in 301/210; the range is set from 1 to 500.

Numeral 305(213) is the band power (the cumulative sum) of the signals in succession for each of the microelectrode recordings in 211.

Number 307(215) displays the continuous root mean square (RMS) calculations for the actual MER signal in 301(210).

Number 309 points to the file information recorded/maintained for the selected file that is being displayed in the top plots (301 and 303). One can select any microelectrode recording along the path in FIGS. 305 and 307. Selecting one of the points will update 301 and 303 and provide the file information (309).

Number 311 points to the newly added function of playing audio of the actual MER recording signals, via the "Listen" button. This adds significantly to the capacity to interpret the signal, not only visually from the plot, but now also aurally.

Number 312 is a function allowing us to save the automatic border detection results to a database via a graphical user interface (GUI). This allows the user to query the "Regions Of Interest" table populated by the automatic border detection algorithms based on the band power (BP) method previously discussed in FIG. 2.

Number 313 shows the functionality button to "Mark" the selected microelectrode recording indicated in 309. When the "Mark" button is actuated, the user is stepped through a process of labeling the file information via GUI's 315, 317, and 319.

Number 314 is function to save the root mean square (RMS) results to the database, presented in FIG. 4 (403), searchable in the "Region Of Interest" table. So, 312 and 314 save information.

Number 315 is the result of selecting or clicking the "Mark" button, presenting the graphical user interface (GUI) which provides the ability to classify, in the database, the region (organelle/tissue type) of the recording that is being observed and marked. After selecting STN, the user can further classify it as top, middle or bottom STN. In this case it is labeled as TOPSTN, because it is the start of the STN (the top) in the progression of the electrode from the point of entry.

Number 317 GUI is spawned after selecting "OK" at reference numeral 315; the GUI at element 317 appears so the user can select the phase of firing seen in that microelectrode recording (MER). There are low, middle and high amplitudes of phase; in this example a label of "High" is selected.

Number 319 is a GUI that appears subsequent to selecting the phase, allowing one to classify the MER data as the initial (more affected) or secondary (less affected) side of the patient's body attached by the disease. This knowledge is acquired from prior visits between the clinician and patient. This process adds valuable patient metadata to the database. If the user doesn't' know the side, indicate "no side."

FIG. 4 illustrates that different ways to store the metadata in tables are provided, such as "Region Of Interest". The software classifies the microelectrode recordings (MER) automatically in the database represented in FIG. 4. All of the information from the MER clips is stored in these tables such as the depth at which it was recorded, the region, the phase, the first affected side, the begin and end times when the particular file was recorded.

The data stored in the table called "Clips" (401) includes the patient identification (ID), record ID, the surgical side, trajectory file name, and the depth. Those pieces of information are enough to classify the microelectrode recordings in a data structure that holds those clips. When the program accesses those files, it uses the "Clip" information to retrieve them.

The "Symptom History" table (402) holds the metadata, such as the first side (or most affected), second side (lesser affected), and the body part first affected, dates and other patient history.

The automatic border detection algorithms mentioned in FIGS. 2 and 3 populates the "Region Of Interest" table (403). The "Files Of Interest" (404) data is populated when the user selects "Mark", as discussed in FIG. 3 (313). The actual clips themselves are not stored in this database, but the referencing information linked to its location is stored here.

The "Distinct Microelectrode Notes" table (405) collects digitized notes taken by the neurologist at each point of interest in the surgery.

The table labeled "Neurology Surgical Notes" (406) stores the general metadata for the patient undergoing surgery.

The data in all of these tables can be cross reference and/or cross-correlated and serves as a powerful tool for research and building knowledge about patients, individually and in aggregate.

FIG. 5 illustrates an example of a digital report of notes that have been entered into the database tables of FIG. 4 (405).

The flow chart in FIG. 6 provides an overview of the process of using the various data sets to create a unique frequency signature base. It begins with the digitized neurologist notes (611) and the patient microelectrode recording (MER) files (612) in parallel. The notes may be queried and the files for those classified as STN or SNr. This query will result in clips that are representative of the organelle of interest. There are two other ways to enter information into the database of representative clips of organelles. One is to mark the microelectrode recording clip (620) using the "Mark" button in FIG. 3 (313). Or, the data can be entered in the database for the organelles via the automatic border detection algorithm, which is discussed and saved using 312 and 314. The result of the organelle automatic border detection algorithm process referred to in FIG. 6 (63) is illustrated by the yellow and red lines in FIGS. 2 (217 and 219, respectively).

The representative organelle MER clips are foundational for the process of signature calculation (610). The next step is to transform the representative MER clips into their frequency spectrums (616). The frequency spectrums are stored in a matrix with all of the clips that are representative of the particular type of target tissue being characterized.

Then, a mathematical process is executed that determines the coherence of the frequencies within all of the selected clips within a set range. The coherence (Z-scores) and average powers are stored for each of those frequencies. A threshold is then applied to the Z-scores; the values with a Z-score above the threshold are kept as representative of the organelle types of interest (619). The process delineated in the flow chart explains how to determine the base of a unique signature. The next steps of the signature creation process are discussed further in subsequent figures.

Figure 7:
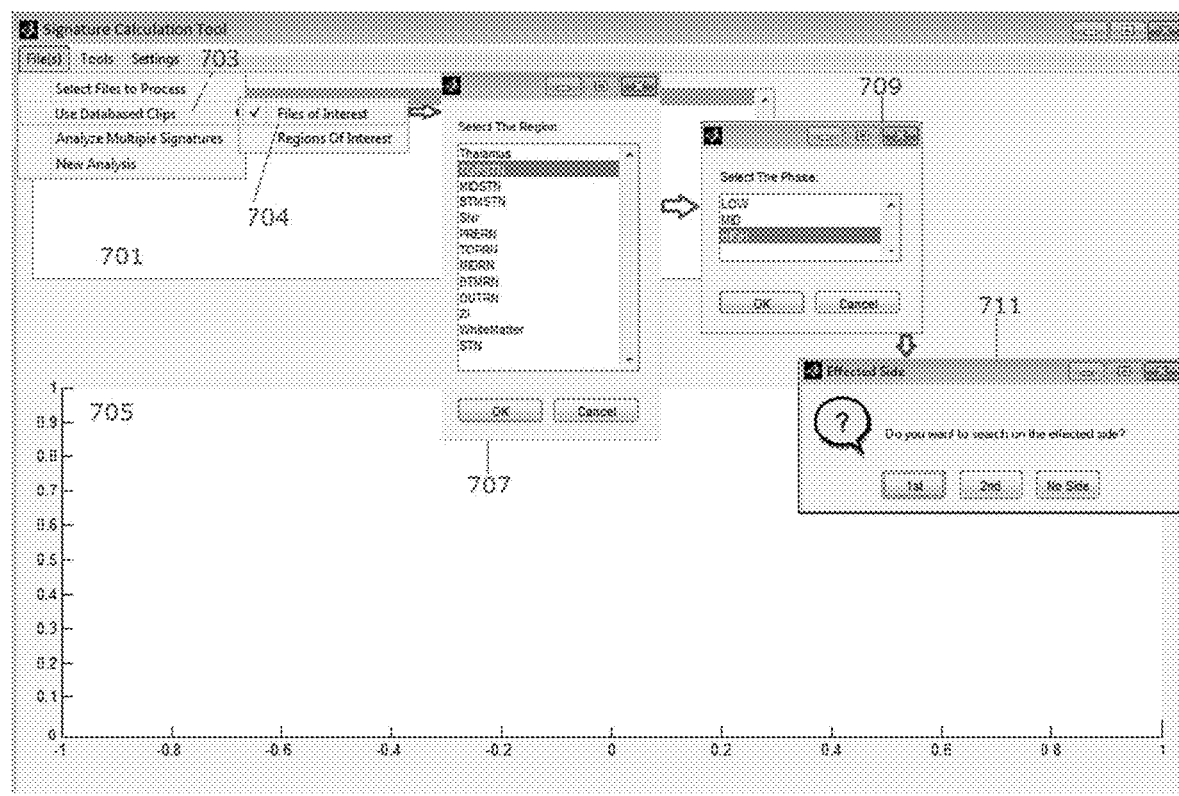
FIG. 7 illustrates sample computer screen capture of the beginning steps performed to create a frequency signature using the Signature Calculation tool.

FIG. 7 shows the actual implementation of the signature creation process using the Signature Calculation program. Using the "Files" tab in the toolbar, "Use Databased Clips" (703) is selected. A drop down menu then appears (704) to select "Files of Interest." This triggers a GUI to "Select the Region" of interest (707). In this figure, TOPSTN is selected. This spawns another GUI (709) to "Select the Phase" of interest and subsequently another (711) that provides the option to search for a first or second side effected.

The Signature Calculation program then searches all of the files in the database and presents those classified by the parameters set by the user. The screen space at 701 indicates where those file names will be populated and 705 is where the signature images will be displayed. The selected files names are also subsequently displayed in FIG. 8.

Figure 8:
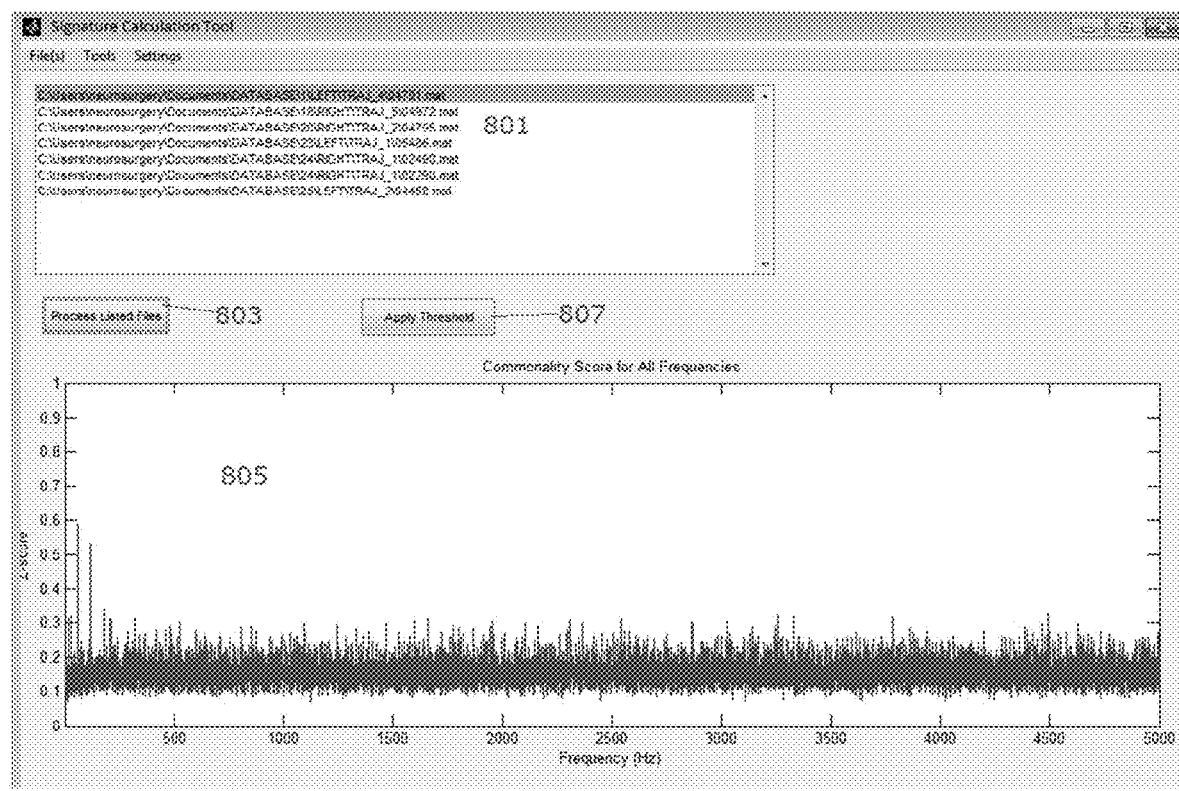
FIG. 8 illustrates a sample computer screen capture of the results of using the Signature Calculation tool with the Top STN region selected, as shown in FIG. 7.

In FIG. 8, reference numeral 801 indicates the list of the files selected via the process described in FIG. 7. Selecting the "Process Listed Files" button (803) runs the Fast Fourier Transform (FFT) for the selected MER files and then implements the coherence function on the calculated frequencies. The outcome of selecting 803 is presented in a plot of the selected files' Z-scores (805), a commonality score for the frequencies from 1 to 5,000 Hertz. After selecting or clicking the "Process Listed Files" button a signature base is created. Next the signature is pared down to something more useful. What is not displayed here is the averaged powers for those respective frequencies that will be shown in other figures. The "Apply Threshold" button (807) removes the frequencies with Z-scores below the threshold. Its outcome is shown in FIG. 9.

Figure 9:
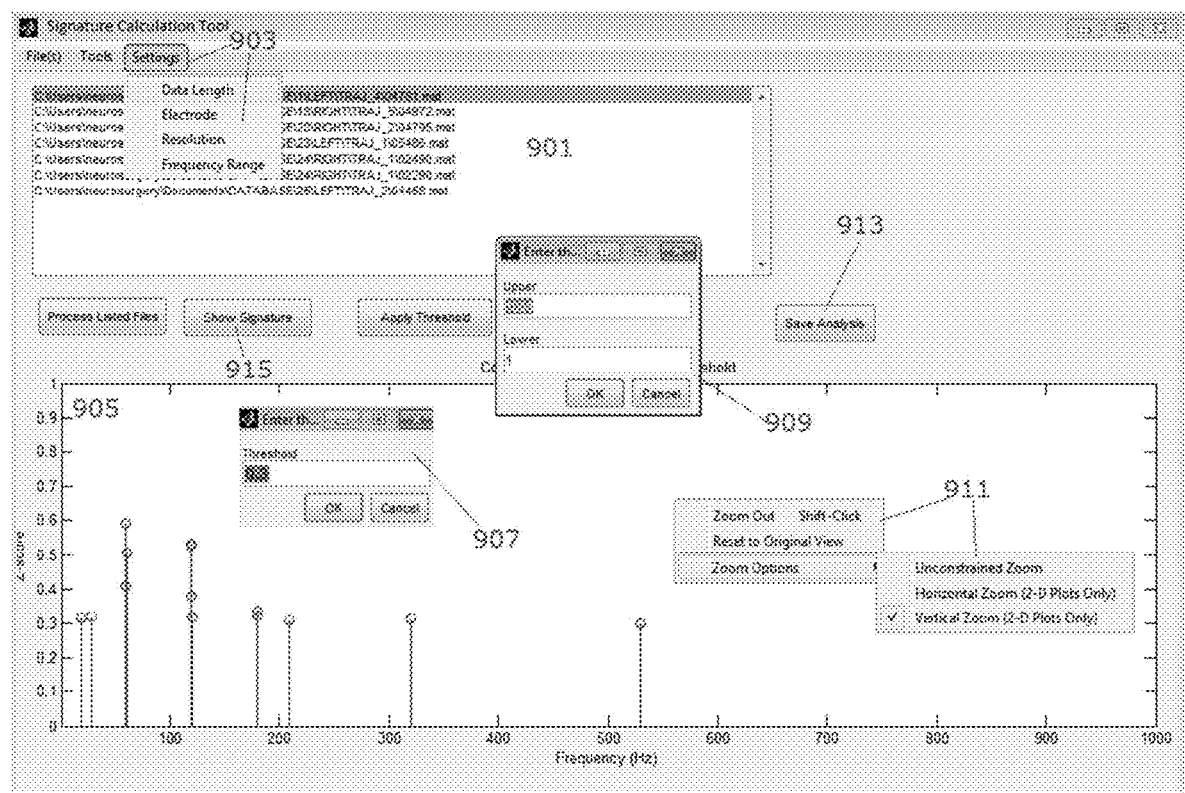
FIG. 9 illustrates a sample computer screen capture of the results of using the Signature Calculation tool to apply or restrict to a selected frequency range and apply a threshold to generate a more unique frequency signature.

FIG. 9 is a composite of multiple options available to the user of the "Signature Calculation" program. Reference numeral 901 indicates the screen space populated by the files returned from the search criteria discussed in FIG. 7. The user has the option on the toolbar under "Settings" to select a frequency range (903). Selecting "Frequency Range" (909) triggers a GUI to set the upper and lower bounds of the frequency range, such as 1 to 1,000, as used here. Using the "Apply Threshold" button (907/807), a threshold of 0.3 was applied. These two steps generate a further refined signature base, shown in the bottom screen space (905). The only elements of the signature base plotted are those with Z-scores above 0.3, in the frequency range of 1 to 1000 Hertz, a reasonable number of values.

Additional options are available to the user via the toolbar.

Under the "Settings" tab (903) the data length may be changed; this changes the amount of raw MER data used in the Fast Fourier Transform (FFT) decomposition. Because the recording files hold data for multiple electrodes, the electrode of interest can also be changed.

Both the "Signature Calculation" tool or program and the "Tissue Signature Detection" tool or program can distinguish or differentiate between frequencies at various levels of resolution. The default resolution is 0.1, but this can be increased or decreased. A smaller resolution takes more computations and therefore more time at multiple stages of use. A balance is struck between fidelity and available computational resources. The ability to zoom in and look at things (911) is included. Zooming in, or out, doesn't affect the signature, but it allows the user to see more clearly what operations would be helpful. The zoom functionality is carried over into FIGS. 10 and 11.

Upon the first presentation of the processed files, the Z-scores are shown so the user can see the commonality (coherence) and start to reveal the signature. The "Show Signature" button (915) will plot the average powers for the frequencies in the set range of the signature.

Via the "Save Analysis" button (913), the signature can be saved using as any file name via the built-in Windows graphical user interface (GUI); this saves the early stage of a signature. The search criteria previously selected (region, the phase, and the first or second side information) was stored and is saved in the signatures files for future use.

In the next phase it is possible to edit further and enhance the signatures' quality, resolution and uniqueness. This is discussed more in FIGS. 10, 11 and 12.

Figure 10:
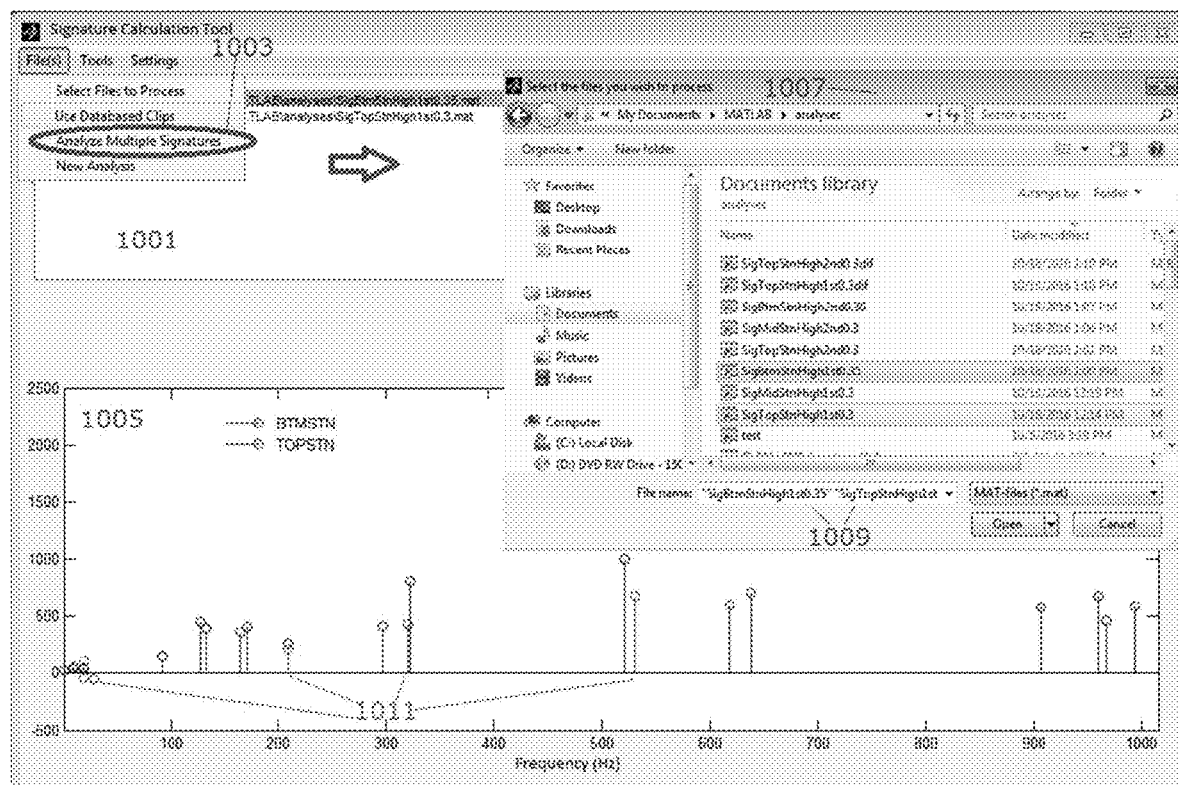
FIG. 10 illustrates a sample computer screen capture of the results of using the Signature Calculation tool to illustrate a further analysis of frequency and power of the signatures for two parts: top and bottom, of the subthalamic nucleus.
Figure 11:
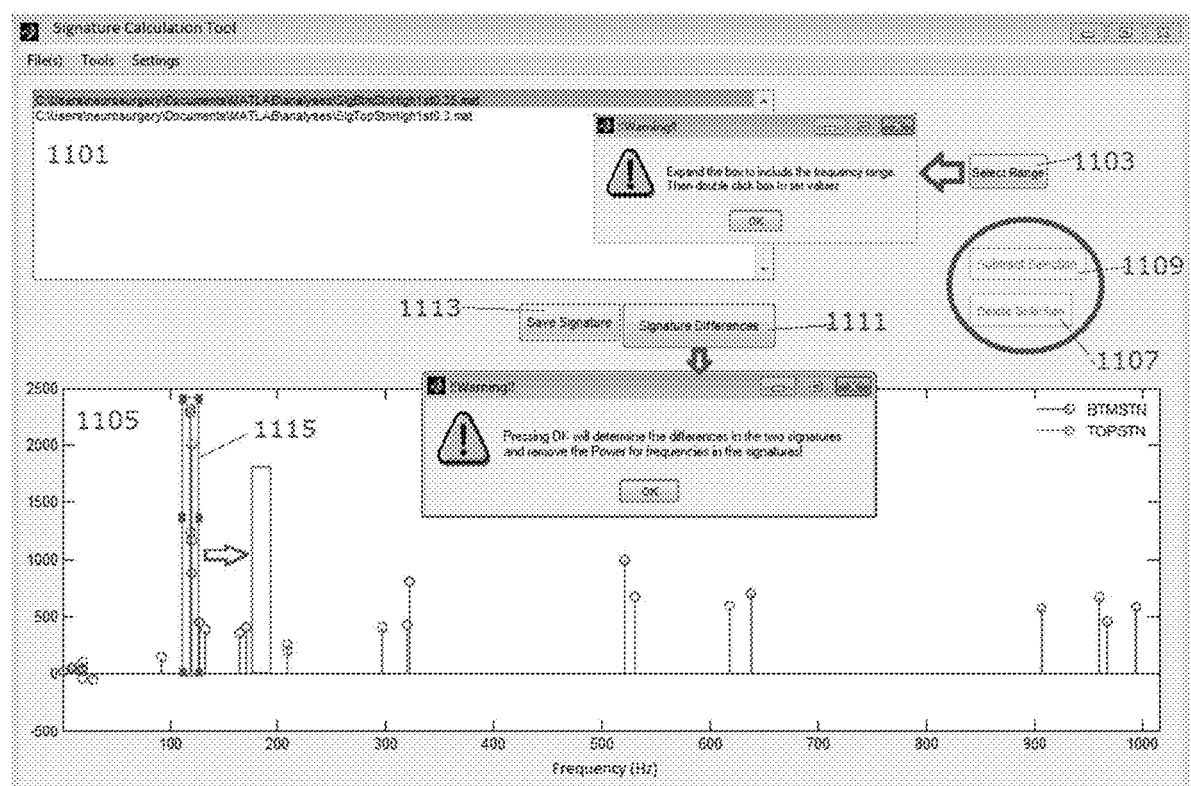
FIG. 11 illustrates a sample computer screen capture of the process or steps of using the Signature Calculation tool to remove irrelevant or non-unique frequency data from the frequency signature of FIG. 10; as well as provides the button to actuate the Signature Differences tool provided in FIG. 12.

FIG. 10 displays a new set of selections from the toolbar in the "Signature Calculation" program. To clear the screen and the internal memory, the user selects "New Analysis" from the "Files" tab. Then, "Analyze Multiple Signatures" (1003) is selected and the user is presented with a built-in Windows GUI menu for selecting individual signature files (1007).

Two signature files are shown as selected to open for further editing (1009). The user can open one or a number of files, limited only by the RAM on one's computer. The actual signature files are shown in 1005. What is being displayed here are the frequencies and average powers of the signatures for two parts of the STN, bottom subthalamic nucleus (BTMSTN) and top subthalamic nucleus (TOPSTN). Reference numeral 1001 illustrates that most of the TOPSTN frequencies (in green) are at the beginning of the frequency band, from 1-500 Hz. The BTMSTN has a number of components in the higher frequency band, ranging from 600-1,000 Hz. Note that there are significant differences with some overlap. At this point additional tools are utilized that are part of this process seen in FIG. 11.

Continuing with the two signatures from FIGS. 10 (1001/1101 and 1005/1105) a number of options are provided. The button at 1103 allows the user to "Select [a] Range" of frequencies within the signature sets. When activated, a warning GUI appears to provide directions on next steps. After pressing OK, the interactive red box (1115) appears around an expandable range of values. Once a range is selected, double clicking will complete the selection process. In this Figure, a range around 120 Hertz is selected, which is a harmonic of 60 Hertz. Both signatures include those frequencies, as do most. Therefore, that frequency is not uniquely characteristic of this organelle's signature. The ranges have been selected that are obviously not unique to delete using the circled "Delete Selection" button (1107). Another warning GUI would appear, if you were to click or press on the button, indicating that the frequency selection will be deleted (not shown). The "Delete Selection" function (1107) is quite useful to remove known issues, such as 60, 120, and 180 Hertz from the signature. The range deletion process has already been performed on 180 Hz, which is the second harmonic of 60. An arrow pointing to the secondary red box (1115) indicates a range around 180, that has been completely deleted (the box is not part of the signature).

The user can do various math calculations on these signatures, such as adding and subtracting frequencies. For example, with 1109 the user could take the two powers, subtract the numbers, and create a new value. Any number of mathematical operations can be performed on the values within the selected range (1103). When new values have been set, the program automatically populates a new plot in the screen space (1105). The "Subtract Selection" function (1109) is distinct from "Delete Selection" (1107), and "Signature Differences" (1111).

All of the previously discussed functionality is incorporated into an automatic process activated by the "Signature Differences" button (1111). There is an arrow to the GUI that appears if 1111 is selected. Pressing OK on this GUI will initiate an algorithm to assess the two signatures (although additional signatures may be included) to determine the difference and remove the frequency information present in both signatures. This is a logical and innovative step-by-step process (delineated in FIG. 12) to take the two signatures and determine what is unique about them and create two new unique signatures in an automatic way.

FIG. 12 shows the mathematical explanation of the "Signature Difference" algorithm for determining a unique signature. This multifaceted algorithm is designed to emphasize the differences in the signatures so that frequencies that are common to the two signatures are minimized and the differences are maximized. The user must be careful with this tool so as not to eliminate frequencies unique to the organelle but common to two sections of the same organelle, for example, with the top STN and the bottom STN. One must use the "Signature Difference" algorithm tool judiciously and sparingly, making sure to not destroy the signatures by being too zealous in removing frequency information.

FIG. 13 illustrates an overview of the signature detection process. The MER analysis Home screen (1350) is where all of the tools are accessible, as discussed in FIG. 2 and FIG. 3. The "Organelle Auto[matic Border] Detection" process (1330) is shown with its relationship to the various pieces. The different plots from the incoming microelectrode recordings (MER), the amplifiers (1352) and filters (1353) of the microelectrodes are shown. When using the "Signature Detection Tool" (1340) the first step for the user is to select the characteristic signatures to search for in the incoming microelectrode recordings (1341).

Figure 14:
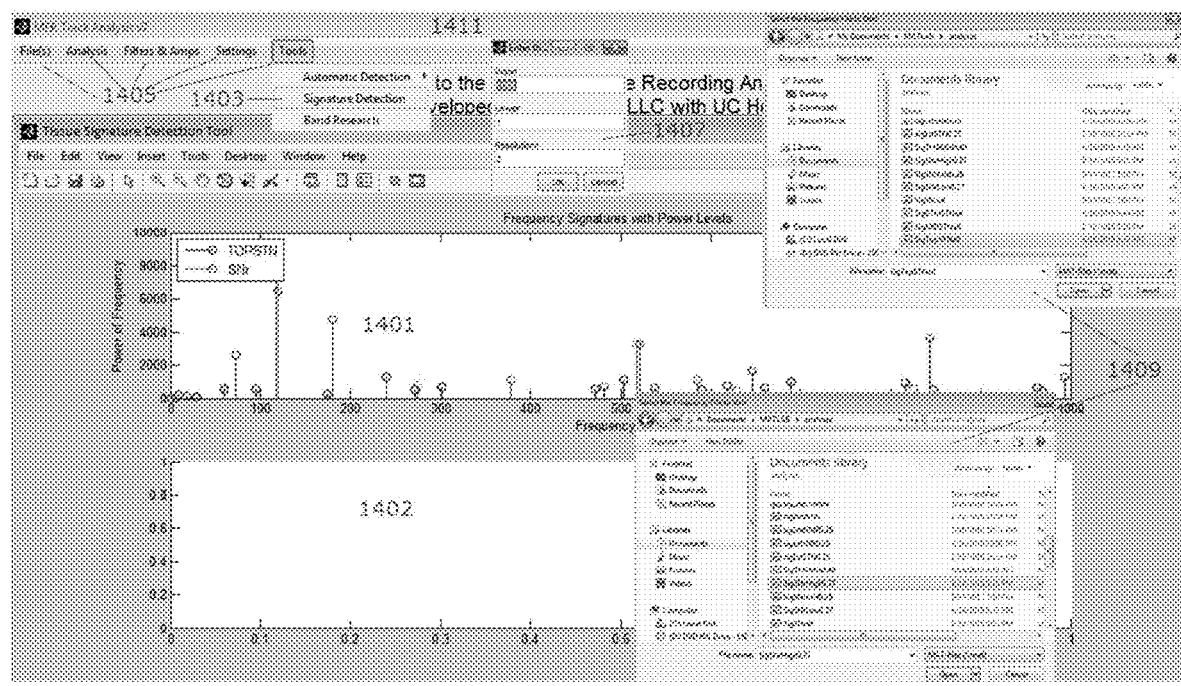
FIG. 14 illustrates a sample computer screen capture showing the set up for use of the Tissue Signature Detection tool.

FIG. 14 is a composite of screen captures of the process to initialize the Tissue Signature Detection tool for use. In this example, the top sub thalamic nucleus (TOPSTN) and the substantia nigra reticulate (SNr) are used. For each incoming microelectrode recording sample, the "Tissue Signature Detection" tool calculates the percent error of the power of the representative signature frequencies, to the power of the incoming signal at the corresponding frequencies and plots the negative of the average percent errors to represent the signature strength (1402/1502).

Element 1411 is representing the supporting structural program discussed in FIGS. 2 and 3, the "MER Track Analysis" program, with its normal options reflected in 1405. From "Tools", the selection of "Signature Detection" turns on the newly added Tissue Signature Detection tool and triggers a GUI (1407) prompting the user to enter a frequency range to limit the signature within. If not changed it will default to pre-set values. Element 1407 also allows for the adjustment of the resolution or bin size used while processing the microelectrode recordings. The bin size or resolution is the breadth of numbers considered the same values in calculations. This is a way to optimize the analysis so it can be in real time and/or allow for a finer, more accurate, resolution.

After setting the variables, the program spawns a Windows file GUI to upload the signatures (1490). One signature is uploaded at a time but the user can select multiple signatures to upload. Element 1401 displays the signatures that are loaded, in this case TOPSTN and SNr. 1402 is where the real time process is going to be displayed.

Figure 15:
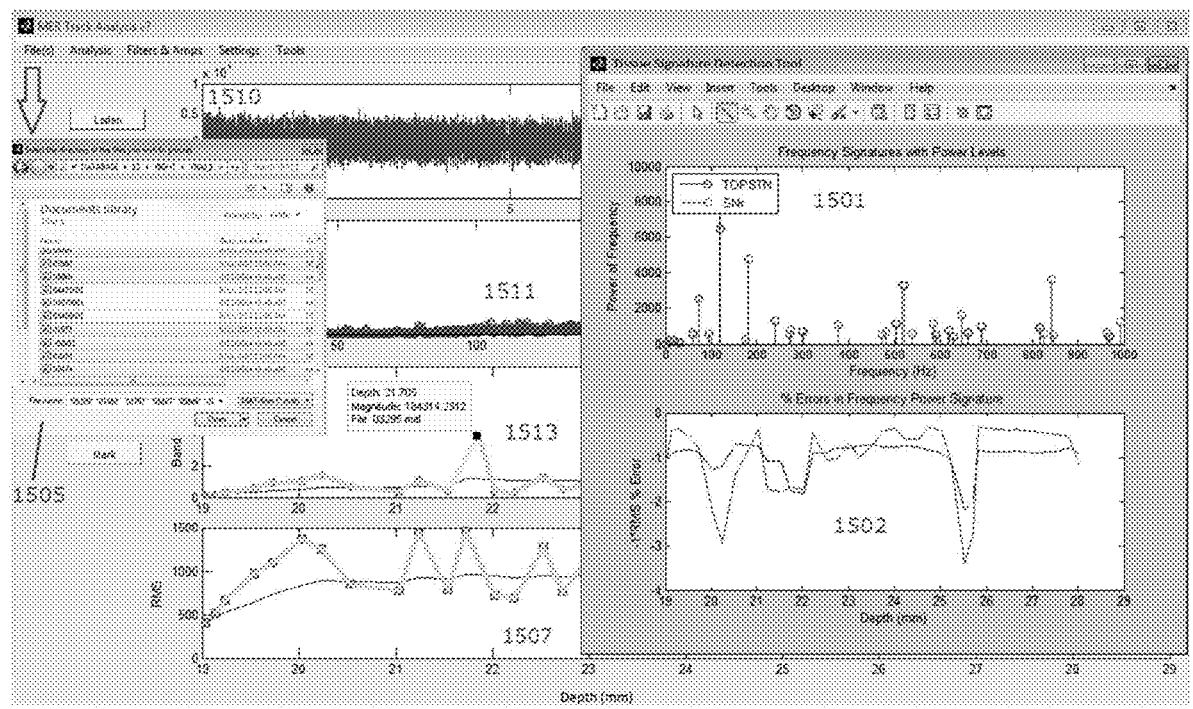
FIG. 15 illustrates sample computer summary screen capture showing the use of the Tissue Signature Detection (TSD) tool as shown in FIG. 1, but with the TSD tool compressed to enable viewing of the continuous MER data analysis, taking place in parallel.

To use the Tissue Signature Detection tool the user follows the same process performed in FIGS. 2 and 3. As before, from the toolbar, select the "File(s)" tab and select a desired batch of microelectrode recording files to open (1505). Upon opening the selected files, the tools are run as in FIGS. 2 and 3. Element 1502 is the plot of the results of the signature detection process. FIG. 15 includes the same plots as FIGS. 2 and 3 (1510/201/301, 1511/211/303, 1513/213/305, 1507/107/215/307). In element 1501(1401), the signatures previously uploaded are seen. The neurosurgical team might not actually want that configuration displayed during surgery. These elements 1501/1401 could easily be removed or turned off if not of use.

In FIG. 15 the Tissue Signature Detection tool (1502) is shown supported by the structure of the prior art software, but could be easily separated from it for independent operation. The actual results are discussed in FIG. 1. In FIG. 1 the supporting structure is not shown as clearly. FIG. 1 stretches out element 1501 & 1502 to reveal the relationship of how it all fits together. Elements 1501 or 1502 could be displayed wherever is convenient and intuitively useful for the neurosurgery team or neurologists.

Alternative Uses or Embodiments

Although the representative frequency signatures are used to recognize brain tissue types being approached, entered, or exited via real time detection within microelectrode recording data, alternative uses are also apparent. One alternate embodiment or use would be as a method to characterize different regions of each tissue type at a finer resolution than presently exists. The method of this application provides for calculating representative signatures for tissue types. In this secondary embodiment, the sub-tissue regions can be further divided and characterized through the methods already described. During the step of selecting the region in signature calculation a more granulated option can be selected. The more granulated regions can be identified during the process of correlating the sub-tissues to the microelectrode recordings (MER) collected as the microelectrode is driven toward the target during DBS surgery. As previously discussed, the pairing can be done three ways: neurologists' notes, automatic detection algorithm, or representative clip marking via the process previously described. Using the method of signature detection is an effective tool for studying the brain. Increasing our understanding of the different kinds of tissue and their function leads to improved quality of care for patients with neurodegenerative diseases and an increased knowledge base to enable further advancements in medicine.

Another embodiment or use would be as a method of more objective and granular levels of diagnosis. When the tissues are identified, they are in varying stages of degradation by the disease; consequently, the representative signatures also change in the progression of the disease. There is a difference between the signatures of the tissue types from the more disease impacted side versus the less affected side of the brain. The disease affects the sub-tissue types differently and these differences can be recognized and then subsequently treated because of this embodiment.

Characterizing and mathematically modeling the changes of disease progression is done by determining the characteristic frequency signature of the more and less affected sides of the brain for each tissue sub-type. These respective signatures are calculated between multiple patients and for each sub-tissue type. Modeling the disease progression is done with respect to time, and in accordance with the following equations, calculations and analyses:

Mathematical Model of Neurological Disease Progression $$D_s = B_s * t + Q_s$$

D means Disease Severity, quantified in equivalent disease years s means tissue type (STN, SNr, GPe, GPi, SNc, STR, RN, THA etc. And/Or More Granulated)

Q means Equivalent Disease Years Experienced t means time $B_s$ means Rate of Change of a Neurological Disease (slope)

Calculated Universal Average Rate of Change of a Neurological Disease for a Given Tissue Type $$\frac{\Delta D_S}{\Delta t} = B_S^U$$

Individual's Disease Progression Profile $$\begin{pmatrix} \Delta B_{STN} \\ \Delta B_{SNr} \\ \Delta B_{GPe} \\ \vdots \\ \Delta B_{CTX} \end{pmatrix}, \begin{pmatrix} Q_{STN} \\ Q_{SNr} \\ Q_{GPe} \\ \vdots \\ Q_{CTX} \end{pmatrix}; \text{ where } \Delta B_S = B_S^{ind.} - B_S^U$$

where $\Delta B_s$ is the difference between the individuals and the universal disease rate of change, for the given tissue type.

Calculating Disease Severity, Quantified in Equivalent Disease Years $$D_s = K_{eq} * C(rE^{Sig.})$$

$$rE^{Sig.} = RMS(\text{Error})^{sig.} = \sqrt{\frac{\sum_{i=1}^{n}(\hat{f}_i - f_i)^2}{n}}$$

$$K_{eq} = \frac{\Delta \text{Equivalant Disease Years}}{\Delta rE^{Sig.}}$$

$K_{eq}$ means experimentally determined universal value

N means Number of frequencies in signature $f_i$ means Frequencies in signature i means Individual Frequency t means time where to means time of assessment; $t_0$ means time of initial disease recognition U means universal parameter
Ind. means an individuals calculated parameter A. $C(rE^{Sig.}) = (rE^{Sig.}_{Healthy} - rE^{Sig.}_{Unhealthy})$ B. $C(rE^{Sig.}) = \left(\dfrac{1}{rE^{Sig.}_{Healthy}} - \dfrac{1}{rE^{Sig.}_{Unhealthy}}\right)$ C. $C(rE^{Sig.}) = \left(\dfrac{rE^{Sig.}_{Unhealthy}}{rE^{Sig.}_{Healthy}}\right)$ D. $C(rE^{Sig.}) = (rE^{Sig}_{Healthy} * rE^{Sig.}_{Unhealthy})$ Having an objective disease progression model of this type enables the recognition of a patient's altered signatures and the respective implications with regard to their disease progression. To use the model, recordings of multiple tissue types of the patient are entered. The data input into this model is the patient's macro electrode recordings (MAR) at the time of assessment, along the lines set forth in FIG. 17. The output would be the disease progression profile. The result is a disease progression profile for each of the individual tissues of the patient at a given moment in time. The disease progression profile includes an objective value of (1) ferocity and (2) damage sustained for each tissue type. With the disease progression profile, it is possible to recognize and diagnose the dynamics of the disease more accurately. With this information, macro electrode recording data (MAR) also stored in 2005, may be read from memory 2001, necessary adjustments calculated in CPU 2000, plotted and displayed to the health care provider for making necessary setting changes. Alternatively, the disease progression calculation may be actuated or triggered automatically upon MAR uploading into the CPU 2000 to accomplish resetting the IPG 2008 via the IPG Programmer 2006 with minimal user input. The results or output of the model is displayed and also saved to a desired aggregate database of patient disease progression information using a simple comma separated file format.

This characterizing and modeling of the changes in disease progression enables us to recognize and diagnose the disease stages more accurately and the different forms of the disease that are not yet fully understood. The accurate measurements of multiple tissue types incorporated in the disease progression profile lead to an objective assessment of the disease. This is in sharp contrast to the subjective assessments used today in the UPDRS Section III assessment tool. Knowing how the different regions degrade within the disease process helps to increase understanding of the disease in general and, therefore, how to treat it effectively, also more precisely (targeted, accurately). These objective measurable changes in disease progression can guide proper treatment, including the need for beam steering via battery settings, modifying drug quantities, drug type, or customized blends of treatments and alternative methods.

Another embodiment or use would be in the practice of precise treatment of patients' unique disease progression patterns. Objective measurable changes in disease progression can guide treatment tailored to the individual including: beam steering, adaptive deep brain stimulation (aDBS), modifying drug quantities, changing drug type, or customizing blends of treatments and alternative methods.

Recent advances in hardware and software design have allowed for macro electrode recording through the signal generator. The energy from the tissue measured in the clinician's office via the implanted macro electrode is the same energy recorded by the microelectrode during DBS surgery. A macro electrode signature would be similar (if not exactly the same) to a signature determined via microelectrode recordings. The representative frequency signatures are detectable within the energy measured by the macro electrode connected to the signal generator. Representative tissue signatures can be calculated through macro electrode signals using techniques for calculating signatures similar to those in the primary embodiment. There might be a small level of refinement needed to translate the microelectrode signatures to the macro electrodes signatures presently exhibited in the patient's brain; but, they would have the fundamental characteristics of those determined via the microelectrode recording method.

The pattern differences between signatures of persons being assessed and the modeled universal patterns can be calculated upon characterizing the universal signature degradation patterns and the disease variations. These calculations would provide a disease progression profile for the patient. Any effects of treatment would be reflected in the patient's disease progression profile. Tracking changes in the disease progression profile enables assessing treatment effectiveness. The disease progression profile includes an objective value of disease (1) ferocity and (2) damage sustained for each tissue type. With the level of detail included in the progression profile the effects of treatments can be recognize at a finer level of resolution than presently available.

Upon quantifying the differences between an individual's frequencies and the disease progression signature model, understanding can be gained enabling the use of those differences to tailor treatment for the individual. Individuals' unique disease progression profile can guide proper treatment, including the need for modifying drug quantities, drug type or alternative methods of treatment. The quality of life of the patients can be improved by more accurately treating their disease. Treating the well characterized disease will lead to fewer drugs and ineffective treatments, thus improving the quality of care and reducing costs.

Another embodiment or use would be in an application or piece of software intended for the training or education of medical professionals, such as neurologists, to help them learn to distinguish the various tissue types visually and/or aurally. The software would display and/or generate an audio signal that includes the representative frequency signature of the tissue of interest superimposed with appropriate levels of noise from surrounding tissues, natural artifacts found in different populations, and artificial artifacts. There is a universal pattern (to a certain extent), in addition to differences based on population groups (e.g., age), as well as characteristics unique to an individual. The signatures would allow them to "listen" and "see" representative signals from people of various ages and sub-populations and their respective signature differences. Diseases progress differently in each population group, these differences can be discerned using the tissue signature detection tool.

Another embodiment would be for use in a computer algorithm or piece of software that expedites the parameter setting process of the internal power generator (IPG) or signal generator (battery) after it has been implanted. If the therapy is effective, the patient's measured signature will mirror a healthier signature. Correspondingly, changes in therapy settings (signal generator values) that are not helpful will lead to more diseased-looking signatures. The parameter finding and setting process can be greatly expedite by merely guiding the caregiver in reducing the disease symptomology.

After electrode placement surgery (DBS) and the subsequent IPG or signal generator (battery) placement surgery, the patient returns to the care team to program the signal generator. At this appointment or set of appointments the IPG or signal generator (battery) is initiated and settings are programmed (parameters set), using an external computer communicating with the internal "battery" via Bluetooth or other wireless technology. The parameters for the signal generator (battery) are fixed to values very commonly used by the clinician and are chosen based on which set demonstrates the most therapeutic effect for the patient.

Figure 16:
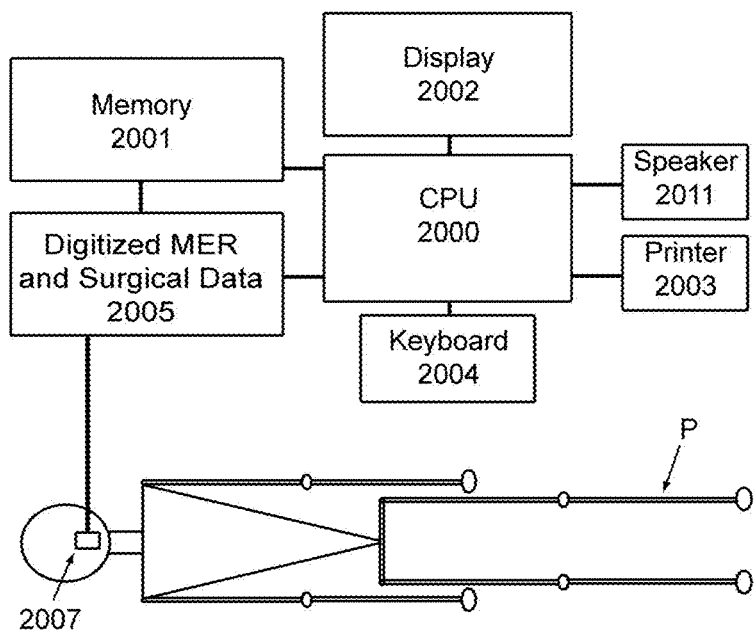
FIG. 16 schematically illustrates components of a system of the present application during DBS surgery.
Figure 17:
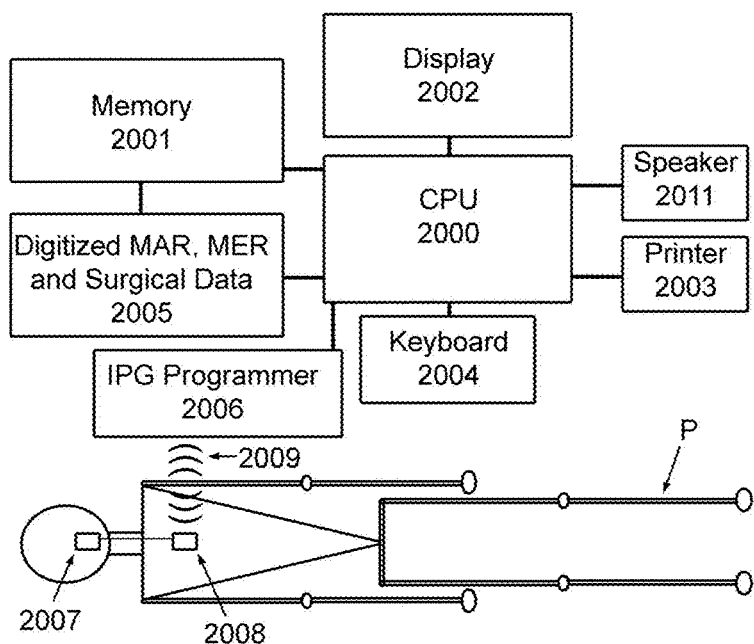
FIG. 17 schematically illustrates components of a system of the present application during IPG programming.

As schematically illustrated in FIGS. 16 and 17, the preferred embodiment of the system used to implement the method of the present application includes a central processing unit (CPU) 2000, a computer readable medium such as a memory 2001, which stores, for example, digitized MER and surgical data 2005. Also included are input devices such as a keyboard 2004 and an implanted electrode 2007. Output devices such as a speaker 2011, printer 2003 and a display monitor 2002 are included, where the results obtained using the method of the present application are displayed and may be viewed by the neurology team. The digitized MER or recorded data 2005 are read from the memory 2001 for processing by the CPU 2000, which is capable of running computer program code comprising instructions for performing the method steps and algorithms according to the present application.

To use Applicant's novel method during an electrode implant surgery, as in the schematic illustration of FIG. 16, MER data is gathered from a patient P via a desired source such as electrode 2007, stored and manipulated as described here, using well known computer hardware and software programs. During use of Applicant's novel method for programming of a previously implanted electrode 2007 using an electronically connected IPG 2008, as in the schematic illustration of FIG. 17, two-way wireless communication, 2009, provides electrode data between the IPG 2008 and an IPG programmer 2006 for processing using the method steps and algorithms according to the present application.

Using techniques for detecting signatures similar to those in the primary embodiment, calculation of the relative strength of tissue signatures via the macro electrode signals is possible. The relative strength can be fed into algorithms or software on a separate device to signal a change or automatically change the parameters or settings, as needed. The therapy applied will modulate the relative signature strength in the underlying tissues. Given that the signatures change for varying degrees of disease, sending the recorded macro electrode signals through an algorithm can create an indicator of whether the patient is achieving therapeutic levels (lesser degree of disease). The connected device or embedded algorithms will independently make the needed changes or indicate the changes needed to be performed by a care giver to optimize therapeutic settings to reproduce healthier-looking tissue signatures, minimizing elements indicative of disease. This configuration would be a real time feedback system that could be adaptable using representative signatures. The representative signatures would be searched for and their respective strengths would be used to calculate a need to modulate the output signals. During initial assessment, the patient will likely start out with a diseased Parkinsonian frequency signature. When the caregiver turns on a particular pattern or setting, a therapeutic level will be achieved when the stimulated tissue no longer emits a diseased signature. This process could be further expedited using an algorithm guiding the caregiver as to the appropriate direction to change the parameter settings, based on intensity changes of the signatures detected. This treatment protocol would, of course, require visual observation, verification, and/or intervention by a neurological health professional at regular follow-up appointments.

Another embodiment or use would be for adaptive DBS or any adaptive form of treatment or therapy using electrodes interacting with brain tissue. The signal generator (battery) is the programming interface for DBS. Presently, the implanted signal generator can be set at different values by the medical caregiver. Changing these settings adjusts the energy pattern transmitted thereby modulating the behavior of the body and mind. These settings (parameter values) can be adaptive (automatically adjusted) via mathematical algorithms to optimize desired effects. These algorithms can be encoded into the software or firmware of the signal generator. The algorithms can have bounds placed on them to ensure that the values are kept within safe therapeutic ranges. Recent advances in hardware and software design have allowed for macro, as well as microelectrode recording through the signal generator.

Another embodiment or use would be to incorporate aDBS in selectable therapeutic modes. Instead of the clinician setting the parameters for the patient based on interactions in the clinic, the patient's activities of daily living would serve as the basis for a menu of multiple mode options. These modes can be preset to therapeutic values by the clinician for activities of the patient's choice, such as sitting, sleeping, walking, sports, and/or others. Each mode can incorporate adaptive DBS. (See previous embodiment.)

Another embodiment or use would be as a basis for a brain/machine interface. A brain/machine interface can be achieved by direct contact via electrodes, as done now. It can, alternatively, be external, via some sort of electromagnetic (EM) energy that would cause some effect inside the brain or cause EM energy patterns to be perceived. There is a transformation of EM energy, via the tissue, during DBS; but the language of the brain is encoded in representative frequency signatures. Just as music lies in the carrier frequency of the radio, so too does the language of the mind lie in the carrier frequency signatures. The representative frequency signatures are merely the carrier frequencies of the underlying information. The "music" and meaning in those carrier signatures can be discovered once the representative frequency signatures are recognized. The "carrier" can be separated from the "music" signal by commonly accepted tools for signal deconvolution.

Another embodiment or use would be to guide replacement of tissue types via a mechanical instrument, physical device, or interface. Using the characteristic frequency signatures as a base, the sub-organelles can be replaced with a mechanical instrument, physical device, or interface that matches or responds appropriately to the frequency signatures of the tissues it normal interrelates with. If the characteristic frequency signature patterns are known, cell or tissue interactions can be used as design specifications. In developing either a mechanical or digital device, the goal would be to replace or augment these signatures. Part of that replacement would be the ability to interface with other tissue: either the actual original tissue or replacement devices. The replacement mechanical instrument, physical device, or interface needs to integrate correctly with the tissue it normally interrelates to; and therefore the communications must be able to generate, interact with, or process the respective signatures.

Another embodiment or use would be as a guide for replication or replacement of tissue types during tissue growth. This embodiment is a method of stem cell differentiation for use in neural cell replacement. The undifferentiated stem cells can be "trained" and manipulated to take the form of the type of cells needed for the specific therapy of interest. Using the characteristic frequency signatures as a base, the sub-organelles can replaced with tissue grown from endogenous or exogenous human stem cells or other species stem cells. If the characteristic frequency signature patterns are known, cell or tissue growth can be guided by stimulating these growing tissues with the appropriate surrounding tissues' signatures; the goal would be to replace or augment these signatures. Part of that replacement would be the ability to interface with other tissue: either the actual original tissue or replacement tissue. The replacement tissue needs to integrate correctly with the tissue it normally interrelates to; and therefore the communications must be able to generate, interact with, or process the respective signatures.

A number of possible routes for distributing the software are viable. As downloadable software it could be made available on a website, via a CD, or any reasonably commonly used method of software distribution. The software could be distributed with other software designed to guide or drive the deep brain stimulation (DBS) electrode. For example, a particular company distributes drive software that controls the mechanical mechanism that delivers the electrode into the brain. It is foreseeable that the representative frequency signatures and the detection software would be provided via that vendor or a similar company and then redistributed with their software. Software packages could be distributed with a configuration file loaded with signatures of interest, such as thalamus, sub-thalamic nucleus (STN), substantia nigra reticulate (SNr), red nucleus (RN) and/or white matter.

Another distribution route would be to lease or rent time to medical teams or training institutions who wish to run the application(s) on a server connected to the internet. There could be an intranet or internet connection enabling access to a local or off-site server hosting the software, where users only pay for the time they are using the software. If distributed as a site license or service license based on time, there could be two foreseeable services performed. One would be setting up a service internally for them that would be maintained by the vendor as part of the license fees. There would be a computer server connected via Ethernet cables that interfaces with the computer receiving the microelectrode recordings during surgery. The other way, via Internet, there would be a server in a convenient location that is maintained by a software team. The customer would upload information and the microelectrode recordings via the internet or private server, depending on the amount of security required. The processing of this information would take place external to the computer being used as a surgical interface. The software could be updated frequently, so the customer would always have access to the most current version. The frequency signature detection software could be, logically, distributed with other software that is involved in electrode placement, such as the drive software. Or it could be distributed separately via individual license where renewal of the license would include upgrades as part of the cost. Or, it could be distributed as a service, with a fee based on units of time that the system is being used. That system could be housed on a server on the internet or intranet, depending on the users' requirements.

While the calculation of representative signature frequencies for tissue types of interest has been described in connection with the various embodiments of the various figures and detailed descriptions, it should be understood that other similar embodiments can also be used or modifications and additions made for performing the same or similar functions without deviating from the disclosed embodiments. For example, one skilled in the art will recognize that the present system and method may be applied using wired or wireless technologies, and may be used on any number of devices connected via a communications network and interacting across a such a network. The embodiments disclosed should be construed in breadth and scope in accordance with the appended claims.

I claim:

1. A computer implemented method for calculating representative frequency signatures for target regions of the brain, comprising the steps of:
    aggregating representative classified microelectrode recordings taken from regions of the brain of multiple patients undergoing deep brain stimulation surgery to an initial database;
    transforming the representative classified microelectrode recordings into a frequency domain;
    storing in a secondary database, frequency profiles selected from the transformed frequencies grouped according to each target region of the brain they represent;
    calculating and storing a coherence or Z-score representing the prominence of a frequency with respect to other frequencies within the group of selected frequency profiles for each target region of the brain they represent, and the average power of the frequencies within the group of selected frequency profiles;
    removing redundant frequencies or frequencies above or below pre-determined thresholds from the group of selected frequency profiles; and
    storing the resulting representative frequency signature for each target region of the brain they represent as a group of frequencies, a coherence or Z-score and an average power of the respective frequencies.

2. The method of claim 1, wherein the step of classifying the microelectrode recordings includes the step of:
    reviewing the microelectrode recordings taken from various regions of the brain of multiple patients undergoing deep brain stimulation surgery and electronically marking each microelectrode recording as recorded within a specific region of the brain.

3. The method of claim 1, wherein the step of removing redundant frequencies or frequencies above or below pre-determined thresholds includes the step of:
    using an automatic signature difference tool to automate removal of redundant or unnecessary frequencies.

4. The method of claim 1, wherein the step of aggregating representative classified microelectrode recordings to an initial database includes the step of:
    reviewing the microelectrode recordings taken from various regions of the brain of multiple patients undergoing deep brain stimulation surgery and electronically marking each microelectrode recording as recorded within a specific region of the brain.

5. The method of claim 1, wherein the step of aggregating representative classified microelectrode recordings to an initial database includes the step of:
    categorizing the microelectrode recordings taken from various regions of the brain of multiple patients undergoing deep brain stimulation surgery using digitized neurological notes to distinguish each microelectrode recording as recorded within a specific region of the brain.

6. The method of claim 1, wherein the step of aggregating representative classified microelectrode recordings to an initial database includes the step of:
   categorizing the microelectrode recordings taken from various regions of the brain of multiple patients undergoing deep brain stimulation surgery using an automatic detection algorithm based on calculating a percent change in microelectrode recordings intensity compared with a baseline calculation of power spectral density (PSD) and root mean square (RMS).

7. A computer implemented method for detecting a target region of the brain using real time microelectrode recordings of brain signals, comprising the steps of:
   pre-selecting desired representative frequency signature file(s) representing target regions of the brain, of which a representative frequency signature file(s) include a list of frequencies, their respective powers, and Z-scores;
   processing real time microelectrode recordings of brain signals from a patient undergoing deep brain stimulation surgery for implantation of a stimulating electrode;
   calculating powers of frequencies of the real time microelectrode recordings at frequencies found in the signatures;
   comparing the calculated powers of frequencies of the real time microelectrode recordings to the respective powers within the pre-selected previously uploaded representative frequency signature files;
   calculating a percent error via the commonly accepted method, and averaging the group of errors via the commonly accepted root mean square calculation; and
   plotting and displaying a negative averaged percent error over time as a measure of frequency signature strength for detecting movement of the stimulating electrode being implanted with respect to the target region of the brain.

8. A computer method for calculating representative frequency signatures for target regions of the brain, comprising the steps of:
   aggregating representative (or classified) microelectrode recordings taken from regions of the brain of multiple patients to an initial database;
   transforming the classified microelectrode recording data into the frequency domain;
   storing in a secondary database the frequencies profiles, grouped according to each target region of the brain they represent;
   calculating and storing a coherence or Z-score representing the prominence of a frequency with respect to other frequencies within a group of frequencies profiles for each target region of the brain they represent, and the average power of the frequencies with-in the group of frequency profiles;
   removing redundant frequencies of frequencies above or below pre-determined thresholds from the group of frequency profiles using an automatic signature difference tool to automate removal of redundant or unnecessary frequencies;
   storing the resulting representative frequency signature for each target region of the brain as a group of frequencies, a coherence or Z-score and an average power of the respective frequencies;
   pre-selecting desired representative frequency signature file(s), previously calculated, representing target regions of the brain, of which a representative frequency signature file(s) include a list of frequencies, their respective powers, and Z-scores;
   processing real time microelectrode recordings of brain signals from a patient undergoing deep brain stimulation surgery for implantation of a stimulating electrode;
   calculating powers of frequencies of the real time microelectrode recordings at frequencies found in the signatures;
   comparing the calculated powers of frequencies of the real time microelectrode recordings to the respective powers within the pre-selected previously uploaded representative frequency signature files;
   calculating a percent error via the commonly accepted method, and averaging the group of errors via the commonly accepted root mean square calculation; and
   plotting and displaying a negative averaged percent error over time as a measure of frequency signature strength for detecting movement of the stimulating electrode being implanted with respect to the target region of the brain.

9. The method of claim 8, wherein the step of classifying the microelectrode recordings includes the step of:
   reviewing the microelectrode recordings taken from various regions of the brain of multiple patients and electronically marking each microelectrode recording as recorded within a specific region of the brain.

10. The method of claim 8, wherein the step of classifying the microelectrode recordings includes the step of:
   categorizing the microelectrode recordings taken from various regions of the brain of multiple patients using digitized neurological notes to distinguish each microelectrode recording as recorded within a specific region of the brain.

11. The method of claim 8, wherein the step of classifying the microelectrode recordings includes the step of:
   categorizing the microelectrode recordings taken from various regions of the brain of multiple patients using an automatic detection algorithm based on calculating a percent change in microelectrode recordings intensity compared with a baseline calculation of power spectral density (PSD) and root mean square (RMS).

12. The method of claim 8, wherein the step of removing redundant frequencies or frequencies above or below pre-determined thresholds includes the step of: using an automatic signature difference tool to automate removal of redundant or unnecessary frequencies.

* * * * *